United States Patent
Demers et al.

(10) Patent No.: US 11,319,944 B2
(45) Date of Patent: May 3, 2022

(54) DISPOSABLE INTERCONNECTED PUMP CASSETTES HAVING FIRST AND SECOND PUMP CHAMBERS WITH VALVED INLET AND OUTLET CONNECTIONS

(71) Applicant: DEKA Products Limited Partnership, Manchester, NH (US)

(72) Inventors: Jason A. Demers, Manchester, NH (US); Larry B. Gray, Merrimack, NH (US); David W. McGill, Woodstock, GA (US); Richard J. Lanigan, Concord, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 308 days.

(21) Appl. No.: 15/966,877

(22) Filed: Apr. 30, 2018

(65) Prior Publication Data

US 2018/0245584 A1 Aug. 30, 2018

Related U.S. Application Data

(63) Continuation of application No. 14/840,591, filed on Aug. 31, 2015, now Pat. No. 9,957,960, which is a
(Continued)

(51) Int. Cl.
*F04B 43/06* (2006.01)
*F04B 53/22* (2006.01)
(Continued)

(52) U.S. Cl.
CPC .............. *F04B 43/06* (2013.01); *F04B 13/02* (2013.01); *F04B 23/02* (2013.01);
(Continued)

(58) Field of Classification Search
CPC ............ F04B 43/0009; F04B 43/0045; A61M 1/0213
See application file for complete search history.

(56) References Cited

U.S. PATENT DOCUMENTS 2,917,465 A 12/1959 Begley
4,056,224 A * 11/1977 Lolachi ............... A61M 1/3693
494/18
(Continued)

FOREIGN PATENT DOCUMENTS

WO WO87/06119 10/1987

OTHER PUBLICATIONS

U.S. Appl. No. 10/696,818, filed Oct. 30, 2003, U.S. Pat. No. 7,354,190.
(Continued)

*Primary Examiner* — Nathan C Zollinger
*Assistant Examiner* — Timothy P Solak
(74) *Attorney, Agent, or Firm* — Michael George Norris

(57) ABSTRACT

A system and method for pumping fluid using a set of interconnected pump cassettes is disclosed. Each of the pump cassettes can receive a first solution in a first pumping chamber and each of the pump cassettes can receive separate second solutions in respective second pumping chambers, so that the first solution can be mixed with the separate second solutions, each said mixture capable of being placed in separate containers. The system includes a control assembly for operating each pump cassette, each pump cassette having a flexible membrane to pump fluid into and out of the pumping chambers, and each pump cassette configured for mating with a base unit that provides positive or negative pneumatic pressure to the flexible membrane.

16 Claims, 23 Drawing Sheets

Related U.S. Application Data continuation of application No. 13/942,282, filed on Jul. 15, 2013, now Pat. No. 9,121,403, which is a continuation of application No. 13/021,532, filed on Feb. 4, 2011, now Pat. No. 8,485,800, which is a continuation of application No. 12/389,646, filed on Feb. 20, 2009, now abandoned, which is a continuation of application No. 10/697,176, filed on Oct. 30, 2003, now abandoned.

(51) Int. Cl.
| | |
|---|---|
| *F04B 53/16* | (2006.01) |
| *F04B 43/00* | (2006.01) |
| *F04B 13/02* | (2006.01) |
| *F04B 23/02* | (2006.01) |
| *F04B 49/22* | (2006.01) |
| *A61M 1/02* | (2006.01) |
| *F04B 23/06* | (2006.01) |
| *F04B 53/06* | (2006.01) |

(52) U.S. Cl.
CPC ......... *F04B 43/0009* (2013.01); *F04B 49/22* (2013.01); *F04B 53/16* (2013.01); *F04B 53/22* (2013.01); *A61M 1/0213* (2014.02); *A61M 2205/125* (2013.01); *F04B 23/06* (2013.01); *F04B 53/06* (2013.01)

(56) References Cited

U.S. PATENT DOCUMENTS

| | | | |
|---|---|---|---|
| 4,161,264 A | 7/1979 | Malmgren et al. | |
| 4,272,824 A | 6/1981 | Lewinger et al. | |
| 4,479,760 A | 10/1984 | Bilstad et al. | |
| 4,650,339 A | 3/1987 | Chetcuti et al. | |
| 4,662,829 A | 5/1987 | Nehring | |
| 4,865,525 A * | 9/1989 | Kern ........................ | F04B 43/02 417/307 |
| 5,062,774 A | 11/1991 | Kramer et al. | |
| 5,098,371 A | 3/1992 | Juji et al. | |
| 5,116,316 A | 5/1992 | Sertic et al. | |
| 5,266,272 A | 11/1993 | Griner et al. | |
| 5,313,992 A * | 5/1994 | Grabenkort ............ | A61J 3/002 137/565.29 |
| 5,324,422 A * | 6/1994 | Colleran ................. | A61M 1/28 210/143 |
| 5,429,485 A | 7/1995 | Dodge | |
| 5,466,220 A | 11/1995 | Brenneman | |
| 5,482,440 A * | 1/1996 | Dennehey ............. | A61M 1/303 417/63 |
| 5,628,908 A | 5/1997 | Kamen et al. | |
| 5,645,531 A * | 7/1997 | Thompson .............. | A61M 5/44 604/67 |
| 5,647,391 A | 7/1997 | Chan et al. | |
| 5,837,905 A | 11/1998 | Strauss et al. | |
| 5,935,332 A | 8/1999 | Caucal | |
| 6,070,761 A | 6/2000 | Bloom et al. | |
| 6,210,361 B1 | 4/2001 | Kamen et al. | |
| 6,214,231 B1 | 4/2001 | Cote et al. | |
| 6,234,997 B1 | 5/2001 | Kamen et al. | |
| 6,245,570 B1 | 6/2001 | Grimm et al. | |
| 6,527,758 B2 | 3/2003 | Ko | |
| 6,605,223 B2 | 8/2003 | Jorgensen et al. | |
| 6,610,040 B1 | 8/2003 | Fowles et al. | |
| 6,796,702 B2 | 9/2004 | Wire et al. | |
| 6,910,797 B2 | 6/2005 | Falcon | |
| 7,011,742 B2 | 3/2006 | Rosiello | |
| 7,544,179 B2 | 6/2009 | Distler et al. | |
| 2002/0045851 A1* | 4/2002 | Suzuki ................... | A61M 1/28 604/28 |
| 2002/0188273 A1* | 12/2002 | Ko ........................ | A61J 3/002 604/403 |

OTHER PUBLICATIONS

U.S. Appl. No. 10/696,893, filed Oct. 30, 2003, U.S. Pat. No. 7,461,968.
U.S. Appl. No. 10/696,969, filed Oct. 30, 2003, U.S. Pat. No. 8,158,102.
U.S. Appl. No. 10/696,984, filed Oct. 30, 2003, US-2005-0095152.
U.S. Appl. No. 10/696,990, filed Oct. 30, 2003, U.S. Pat. No. 7,632,078.
U.S. Appl. No. 10/697,176, filed Oct. 30, 2003, US-2005-0095141.
U.S. Appl. No. 10/697,450, filed Oct. 30, 2003, U.S. Pat. No. 7,632,080.
U.S. Appl. No. 10/697,862, filed Oct. 30, 2003, U.S. Pat. No. 7,662,139.
PCT/US04/35952, Oct. 29, 2004, WO2005/044435.
PCT/US04/35970, Oct. 29, 2004, WO2005/044337.
PCT/US04/36144, Oct. 29, 2004, WO2005/042139.
U.S. Appl. No. 11/926,646, filed Oct. 29, 2007, US-2008-0108968.
U.S. Appl. No. 11/926,777, filed Oct. 29, 2007, US-2008-0138223.
U.S. Appl. No. 11/926,891, filed Oct. 29, 2007, U.S. Pat. No. 7,993,050.
U.S. Appl. No. 11/926,992, filed Oct. 29, 2007, U.S. Pat. No. 7,874,718.
U.S. Appl. No. 11/927,081, filed Oct. 29, 2007, US-2008-0113331.
U.S. Appl. No. 11/927,101, filed Oct. 29, 2007, U.S. Pat. No. 7,726,362.
U.S. Appl. No. 12/258,823, filed Oct. 27, 2008, U.S. Pat. No. 7,959,196.
U.S. Appl. No. 12/389,646, filed Feb. 20, 2009, US-2009-0185920.
U.S. Appl. No. 13/021,532, filed Feb. 4, 2011, U.S. Pat. No. 8,485,800.
U.S. Appl. No. 13/942,282, filed Jul. 15, 2013, U.S. Pat. No. 9,121,403.
U.S. Appl. No. 14/840,591, filed Aug. 31, 2015, U.S. Pat. No. 9,957,960.

\* cited by examiner

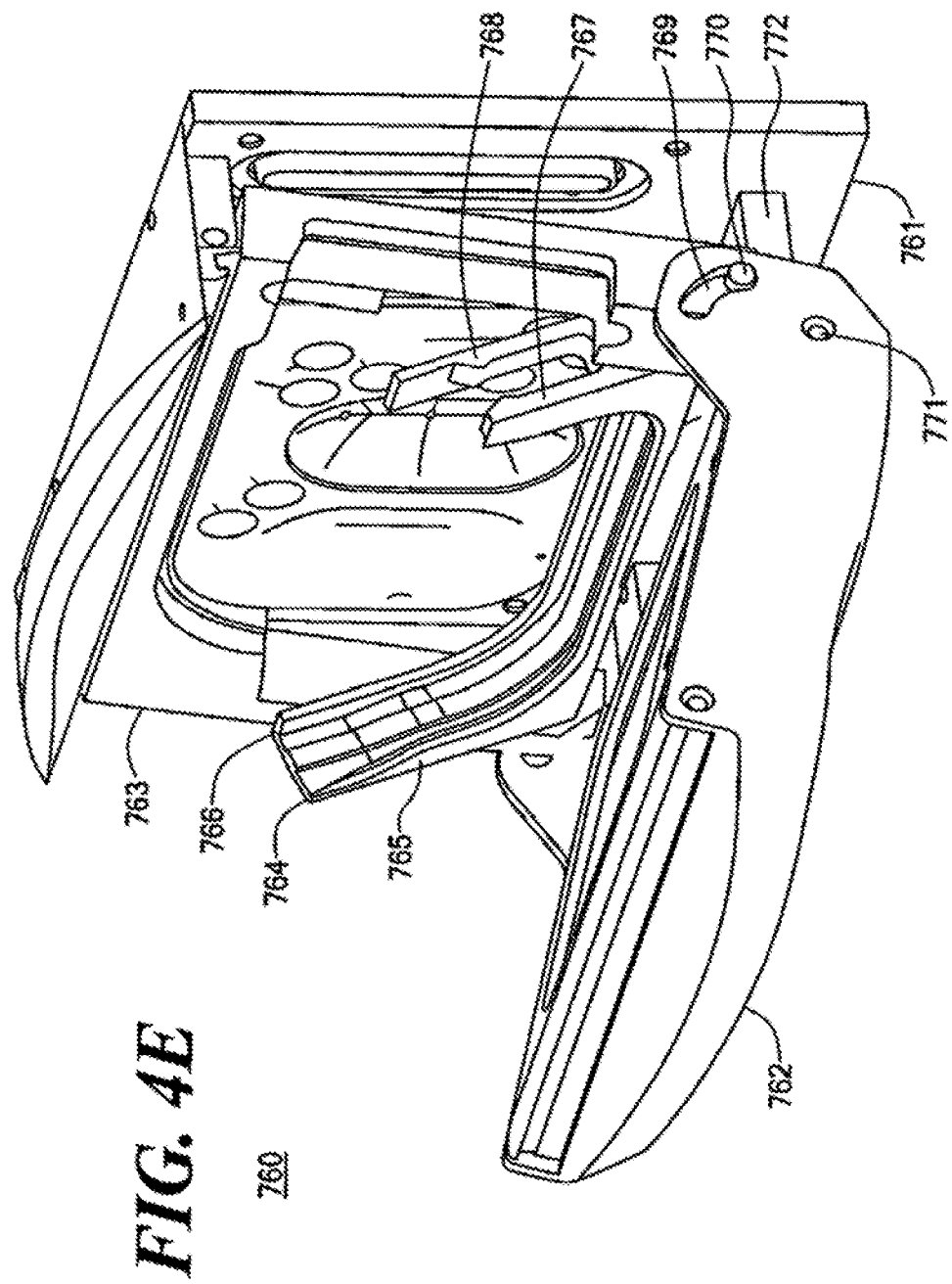

DISPOSABLE INTERCONNECTED PUMP CASSETTES HAVING FIRST AND SECOND PUMP CHAMBERS WITH VALVED INLET AND OUTLET CONNECTIONS

CROSS REFERENCE TO RELATED APPLICATIONS

The present application is a continuation of U.S. patent application Ser. No. 14/840,591, filed Aug. 31, 2015, now U.S. Pat. No. 9,957,960, issued May 1, 2018 and entitled "SYSTEM FOR SEALING A PUMP CASSETTE AGAINST A CASSETTE CONTROL ASSEMBLY", which is a continuation of U.S. patent application Ser. No. 13/942,282, filed Jul. 15, 2013, now U.S. Pat. No. 9,121,403, issued Sep. 1, 2015 and entitled "SYSTEM AND METHOD FOR PUMPING FLUID USING A PUMP CASSETTE", which is a continuation of U.S. patent application Ser. No. 13/021,532, filed Feb. 4, 2011, now U.S. Pat. No. 8,485,800, issued Jul. 16, 2013 and entitled "SYSTEM AND METHOD FOR PUMPING FLUID USING A PUMP CASSETTE", which is a continuation of U.S. patent application Ser. No. 12/389,646, filed Feb. 20, 2009,now abandoned, entitled "SYSTEM AND METHOD FOR PUMPING FLUID USING A PUMP CASSETTE", which is a continuation of U.S. patent application Ser. No. 10/697,176, filed Oct. 30, 2003, entitled "SYSTEM AND METHOD FOR PUMPING FLUID USING A PUMP CASSETTE", now abandoned, all of which are incorporated by reference herein in their entireties.

U.S. patent Application Ser. No. 14/840,591, filed Aug. 31, 2015, now U.S. Pat. No. 9,957,960, issued May 1, 2018 and entitled "SYSTEM FOR SEALING A PUMP CASSETTE AGAINST A CASSETTE CONTROL ASSEMBLY", may include subject matter related to one or more of the following commonly-owned United States patent applications, each of which was filed Oct. 30, 2003 and is hereby incorporated herein by reference in its entirety:

U.S. Pat. No. 8,158,102 entitled SYSTEM, DEVICE, AND METHOD FOR MIXING A SUBSTANCE WITH A LIQUID (referred to herein as "Application D70");

U.S. Pat. No. 7,461,968 entitled SYSTEM, DEVICE, AND METHOD FOR MIXING LIQUIDS (referred to herein as "Application D71");

U.S. Pat. No. 7,354,190 entitled TWO-STAGE MIXING SYSTEM, APPARATUS, AND METHOD (referred to herein as "Application D72");

U.S. patent application Ser. No. 10/696,984 entitled DOOR LOCKING MECHANISM, now abandoned (referred to herein as "Application D74");

U.S. Pat. No. 7,632,080 entitled BEZEL ASSEMBLY FOR PNEUMATIC CONTROL (referred to herein as "Application D75");

U.S. Pat. No. 7,662,139 entitled PUMP CASSETTE WITH SPIKING ASSEMBLY (referred to herein as "Application D84"); and U.S. Pat. No. 7,632,078 entitled PUMP CASSETTE BANK (referred to herein as "Application D85").

FIELD OF THE INVENTION

The present invention relates generally to pumping and/or mixing of fluids, and more particularly to a system and method for pumping and/or mixing of fluids using a pump cassette.

BACKGROUND

Pneumatic pumping devices using pump cassettes are known in the art. Among other things, pump cassettes typically include various membrane-based chambers and valves that are pneumatically actuated by a control assembly. During use, the control assembly is aligned and pressed in very close face-to-face contact against the pump cassette. Such alignment and contact permit the control assembly to precisely actuate the cassette chambers and valves, thus regulating fluid flow through the cassette. Precise actuation permits the overall pumping device to pump precise amounts of fluid.

To those ends, the control assembly typically includes a front surface that is sealingly pressed against a rear surface of the pump cassette. The front surface of the control assembly includes membranes that align with chambers and valves in the cassette. The membranes in the control assembly are pneumatically controlled to inflate and deflate in a manner that precisely controls operation of corresponding valves and chambers in the cassette.

During operation, it is important to ensure appropriate sealing alignment and close face-to-face contact between the cassette and control assembly. Improper spacing, sealing, or alignment between the control assembly and cassette undesirably can impact the precision with which the cassette chambers are expanded and contracted. Consequently, the fluid amounts pumped by the cassette can be inaccurate.

SUMMARY OF THE INVENTION

In accordance with one aspect of the invention, a system for pumping fluid using a pump cassette is presented. The system includes a control assembly for operating the pump cassette. A force assembly has a movable member capable of applying force to the pump cassette, to press the pump cassette against the control assembly.

In accordance with related embodiments of the invention, the movable member includes an expandable member that is capable of expanding, such as a bladder. Expansion of the expandable member presses the pump cassette against the control assembly. The force member may include a door, the movable member coupled to the door. The force member may include a back plate and a frame, with the movable member positioned between the back plate and the frame. The system may include a pneumatic circuit for controlling the movable member. The movable member may be coupled to a piston assembly which is capable of contacting the pump cassette.

In accordance with further related embodiments of the invention, the system may include a cassette receptacle for receiving the pump cassette. The force assembly may be movably coupled to the control assembly to allow access to the cassette receptacle. For example, the force assembly may be pivotally coupled to the control assembly, or may move in a linear fashion away from the control assembly. The cassette receptacle may be movably coupled to the force assembly and/or control assembly to allow further accessibility.

In still further related embodiments of the invention, the control assembly includes a bezel and a bezel gasket. The bezel gasket includes a membrane capable of being displaced to operate the pump cassette. The control assembly may include a rigid and/or fixed plate to which the bezel is attached.

In accordance with another aspect of the invention, a method of pumping fluid using a pump cassette is presented. The method involves providing the pump cassette and providing a control assembly capable of operating the pump cassette. The pump cassette is inserted into a cassette receptacle. A movable member is moved against at least one of the cassette receptacle and pump cassette to press the pump cassette against the control assembly.

In accordance with related embodiments of the invention, the movable member is capable of expanding. Moving of the movable member includes expanding the movable member to press the pump cassette against the control assembly. Expanding the movable member may be performed pneumatically. The method may further include pumping at least one fluid through the pump cassette. In various embodiments, at least two fluids are mixed together within the pump cassette. Inserting the pump cassette into the receptacle may include opening a door on the control assemble to gain access to the cassette receptacle, the movable member attached to the door.

In accordance with another embodiment of the invention, a system for pumping fluid using a pump cassette includes means for operating the pump cassette. The system also includes operating means for applying force to the pump cassette to press the pump cassette against the operating means.

In accordance with related embodiments of the invention, the means for applying force to the pump cassette includes an expandable member, such as a bladder, that is capable of expanding to press the pump cassette against the operating means. The operating means may include a bezel and a bezel gasket capable of being displaced to operate the pump cassette. The system may include a pump cassette receptacle for receiving the pump cassette. The means for applying force to the pump cassette may be movably coupled to the operating, to allow access to the cassette receptacle.

BRIEF DESCRIPTION OF THE DRAWINGS

FIG. 4E shows an exemplary door assembly including a positive release mechanism in accordance with an alternate embodiment of the present invention;

DETAILED DESCRIPTION

Illustrative embodiments of the present invention pump fluid using a pump cassette. The pump cassette, which is preferably pneumatically operated by a control assembly, includes various combinations of membrane-based chambers and valves. During use, the control assembly is pressed in close face-to-face contact against the pump cassette, and precisely actuates the membrane-based chambers and valves to regulate fluid flow through the cassette. A force assembly ensures that an adequately sealed, face-to-face contact is maintained between the control assembly and the pump cassette. To those ends, the force assembly includes a movable member capable of applying a continuous force to the pump cassette to press the pump cassette against the control assembly. Details of various embodiments are discussed below.

Figure 1:
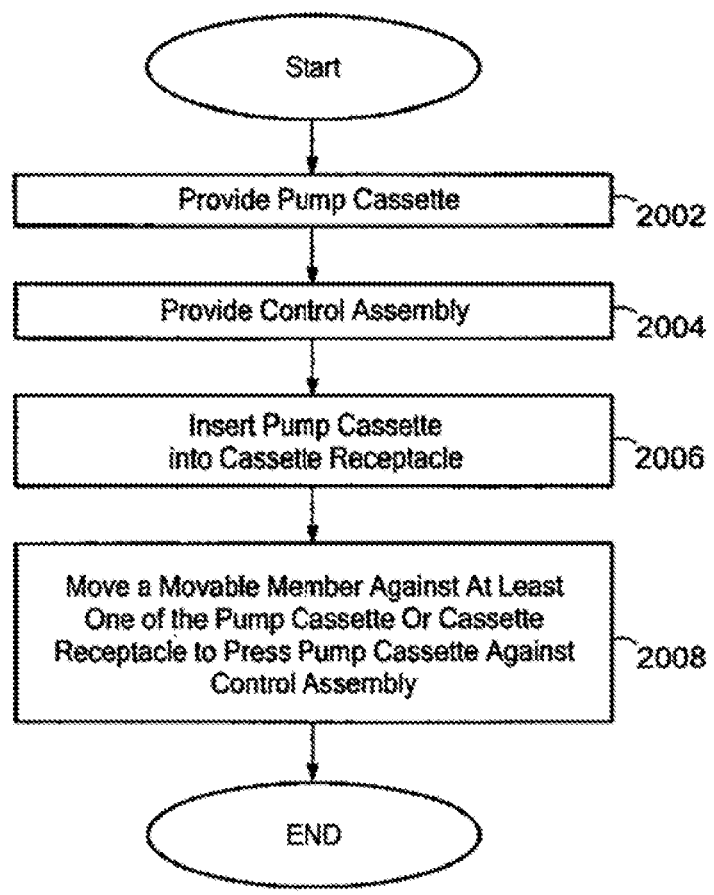
FIG. 1 is a process flow diagram describing a process for pumping fluid using a pump cassette in accordance with an embodiment of the present invention.

FIG. 1 is a process flow diagram describing a process for pumping of fluid using a pump cassette, in accordance with one embodiment of the invention. Beginning in block 2002, a pump cassette is provided, which may be disposable. As described above, the pump cassette includes various pump chambers and various valves, which are preferably operated pneumatically.

Figure 2A:
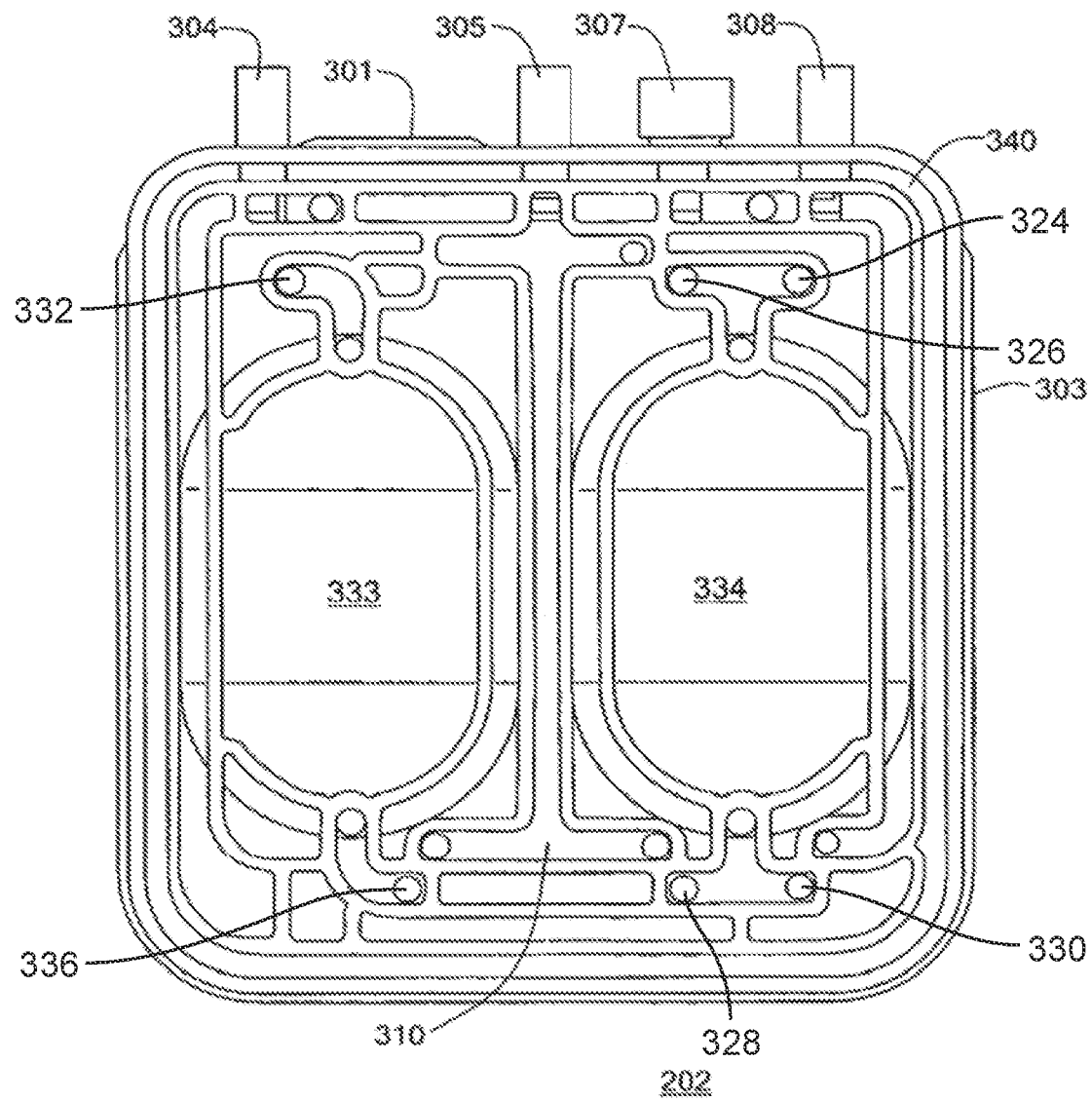
FIG. 2A shows a front view of the pump cassette in accordance with an embodiment of the present invention.

FIG. 2A shows a front view of an exemplary pump cassette 202 in accordance with an embodiment of the present invention. The pump cassette 202 is essentially a rigid core including formations and sealing ribs 340 constituting the various ports 304, 305, 307 and 308, pumping chambers 333 and 334, valves, and fluid pathways (channels) 310. The rigid core is covered on each side by a flexible membrane, which may be, without limitation, a flexible PVC sheet. The flexible membranes seal against the core and isolate the control assembly from fluids within the cassette. The pump cassette 202 is typically designed to interface with the control assembly in only one direction. For example, the pump cassette 202 typically includes an asymmetric feature, such as placement of tubing, or other interlock that prevents the pump cassette 202 from being inserted into the system incorrectly. The pump cassette 202 preferably includes a top rib 301 that limits vertical travel of the pump cassette 202 when the pump cassette 202 is installed in a pump as well as a peripheral rib 303 extending along portions of the sides and bottom of the pump cassette 202 that is used to hold the cassette within a cassette receptacle, as described below. The top rib 301 and the peripheral rib 303 is shown in greater detail in FIG. 2C.

Figure 2B:
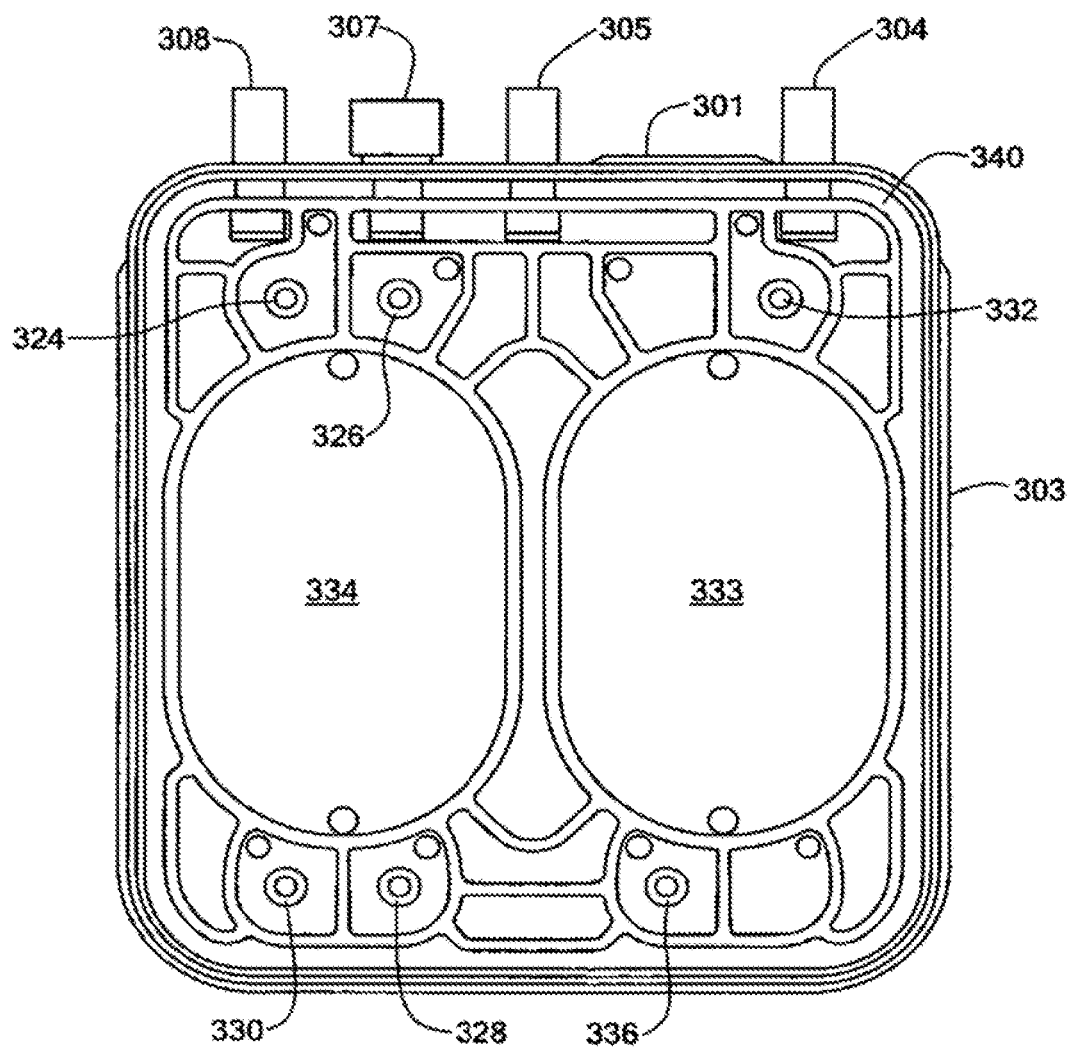
FIG. 2B shows a rear view of the pump cassette in accordance with an embodiment of the present invention.
Figure 2C:
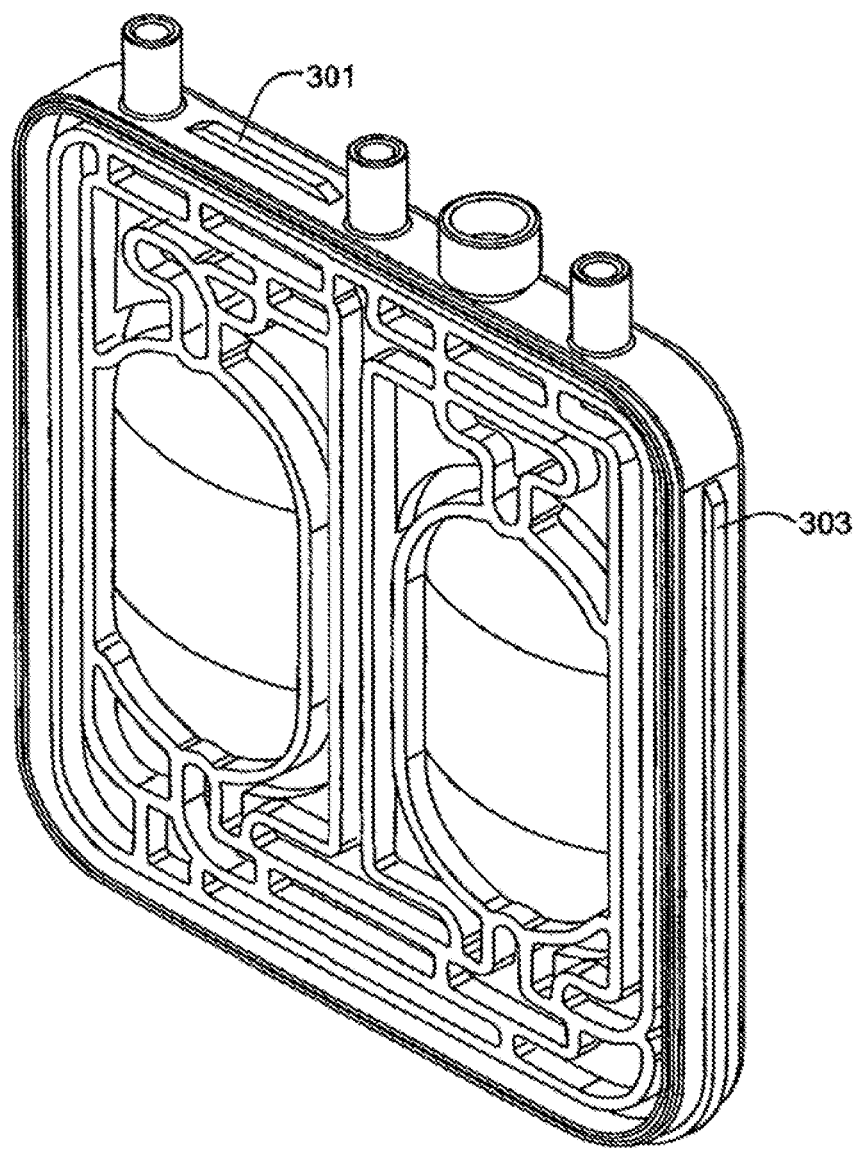
FIG. 2C shows a perspective view of the pump cassette in accordance with an embodiment of the present invention.

FIG. 2B shows a rear view of the pump cassette 202 in accordance with an embodiment of the present invention. The rear view of the pump cassette 202 shows various "volcano" valves 324, 326, 328, 330, 332 that are used to open and close various fluid pathways within the pump cassette 202. The volcano valves and the pumping chambers are all operated pneumatically from the rear of the pump cassette 202, as discussed below.

Referring back to FIG. 1, the process continues to step 2004 by providing a control assembly capable of operating the pump cassette 202. The control assembly includes pneumatic pathways that interface with a receiving surface through which the pump cassette 202 is operated. The receiving surface may be, without limitation, a bezel gasket that is part of a bezel assembly. During operation, the pump cassette 202 is aligned and pressed against the bezel gasket by a movable member, as discussed below. Air lines connected to the bezel assembly are controlled pneumatically, and used to displace membranes of the bezel gasket to operate the various valves and chambers of the pump cassette 202.

Figure 3A:
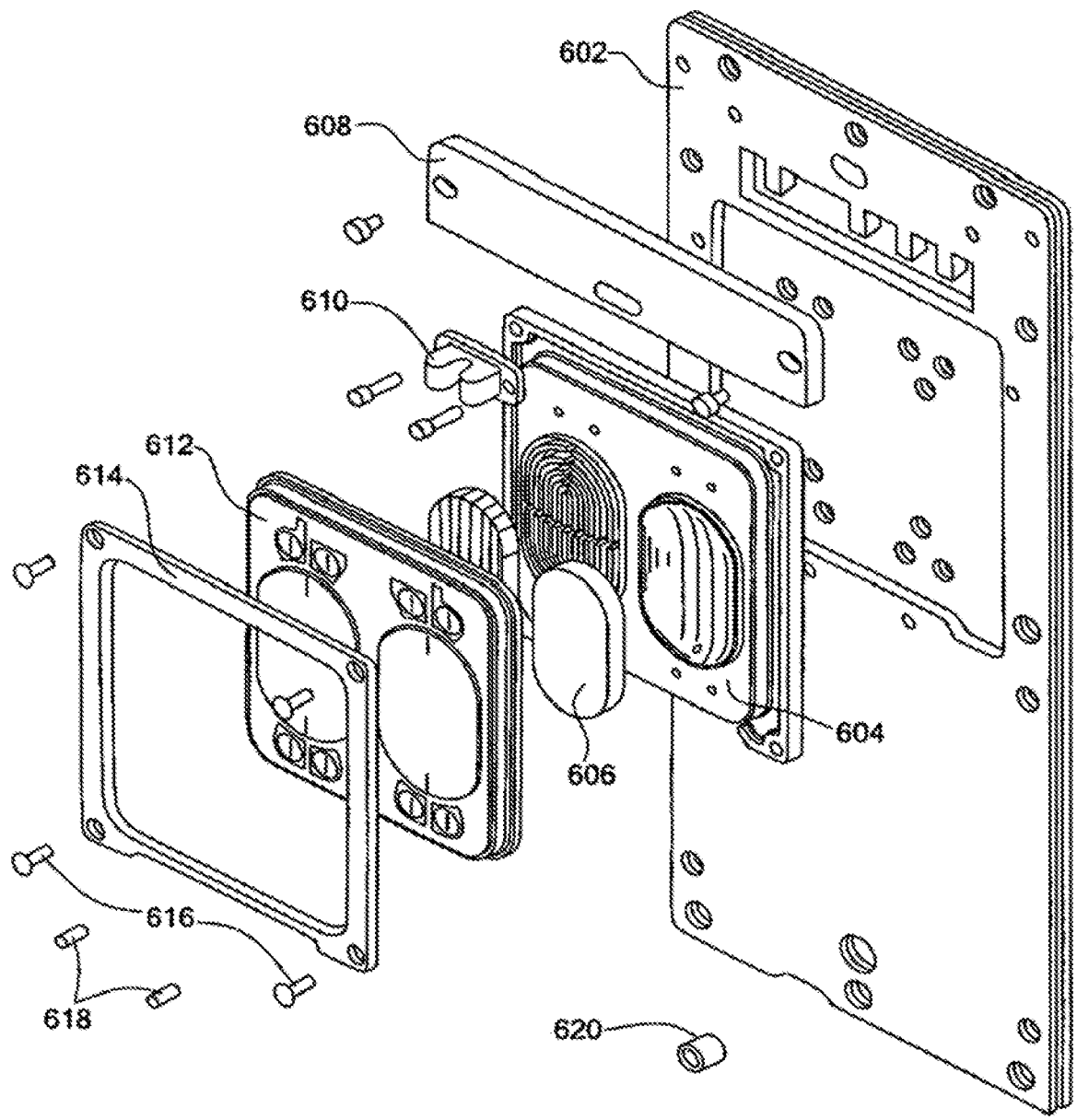
FIG. 3A shows an exploded view of an exemplary control assembly in accordance with an embodiment of the present invention.

FIG. 3A shows an exploded view of an exemplary control assembly 408 in accordance with an embodiment of the present invention. Among other things, the control assembly 408 may include a rigid front plate 602 to which are mounted a bezel 604, chamber foam 606, spacer 608, air-in-line sensor 610, bezel gasket 612, gasket retainer 614, hardware 616, dowel pins 618, and grommet 620. The bezel 604, chamber foam 606, and bezel gasket 612 are mounted to the front plate 602 by the gasket retainer 614 and associated hardware 616, forming the control assembly 408. The front plate 602 is generally rigidly attached to the pump chassis, helping to prevent deformation of the bezel 604 and bezel gasket 612 during the pumping operation. Additionally, the front plate 602 includes holes for allowing air tubes to pass between the rear of the bezel 604 and a pneumatic control assembly, which is typically situated behind the front plate 602. The front plate 602 may also include openings for occluder blades and for engaging a door latch mechanism, as described below. Air-in-line sensor(s) 610 can be used for example, to detect air in various tubes 204.

Figure 3B:
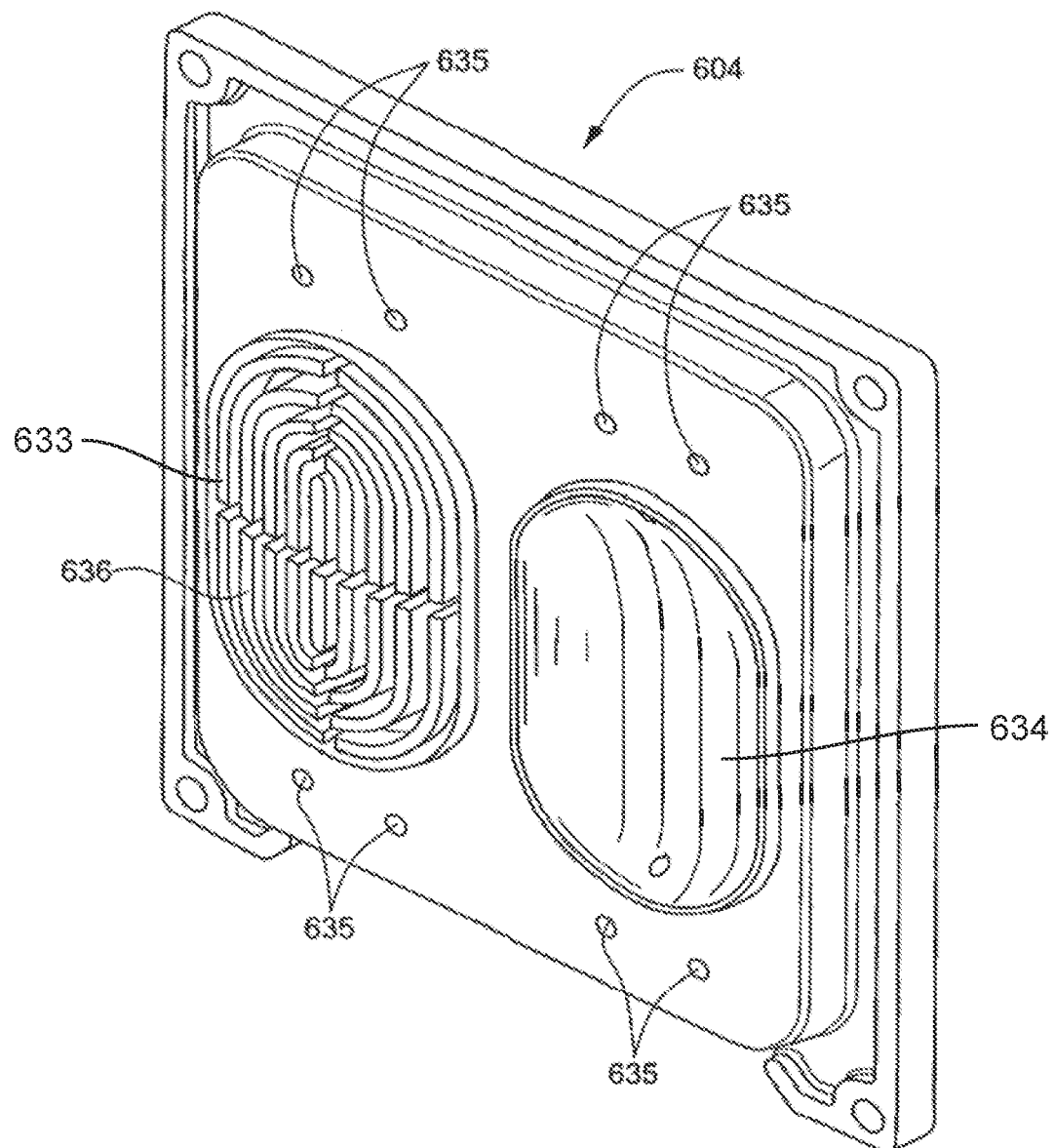
FIG. 3B shows a front view of an exemplary bezel in accordance with an embodiment of the present invention.

FIG. 3B shows a front view of an exemplary bezel 604 in accordance with an embodiment of the present invention. The bezel 604 may be made of various materials such as, without limitation, plastic or various metals. In various embodiments, the bezel 604 is a molded polycarbonate/ABS unit. The bezel 604 includes various chambers for operating corresponding chambers and valves of the pump cassette. With respect to the pump cassette 202 discussed above, chamber cavity 633 operates chamber 333 of the pump cassette 202, chamber cavity 634 operates chamber 334 of the pump cassette 202, and various valve cavities 635 operate the various valves of the pump cassette 202. Certain cavities 633 may be molded with rib structures 636 that allow for airflow within the cavity 633, but mechanically restrict the amount of working solution that can be drawn into the chamber 333 of the pump cassette 202. Alternatively, ribs may not be utilized, allowing for greater pumping capacity. The bezel is described in greater detail in Application D75.

Figure 3C:
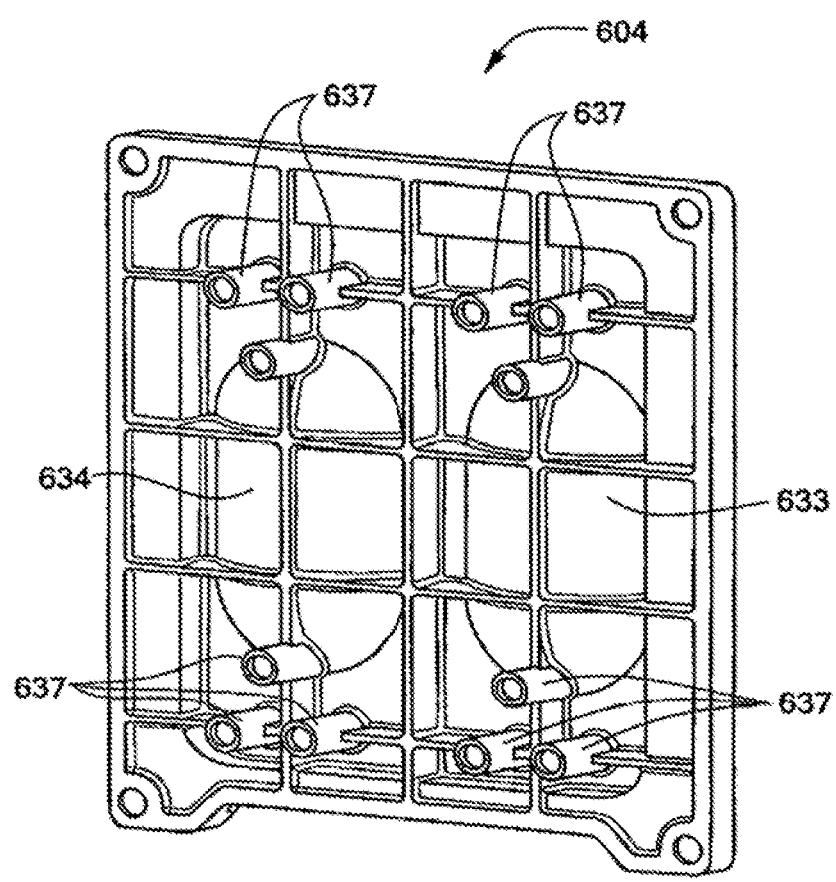
FIG. 3C shows a rear view of an exemplary bezel in accordance with an embodiment of the present invention.

FIG. 3C shows a rear view of the bezel 604 in accordance with an embodiment of the present invention. The bezel 604 includes connections, which may be integral solvent bondable tubing connections (ports) 637, to which pneumatic tubing from a pneumatic control assembly are connected. In this embodiment, each of the valve cavities 635 is associated with a single integral port 637, and each of the chamber cavities 633 and 634 are associated with two integral ports 637. The integral ports 637 allow the pneumatic connections to be made without independent fittings and accompanying O-rings.

Figure 3E:
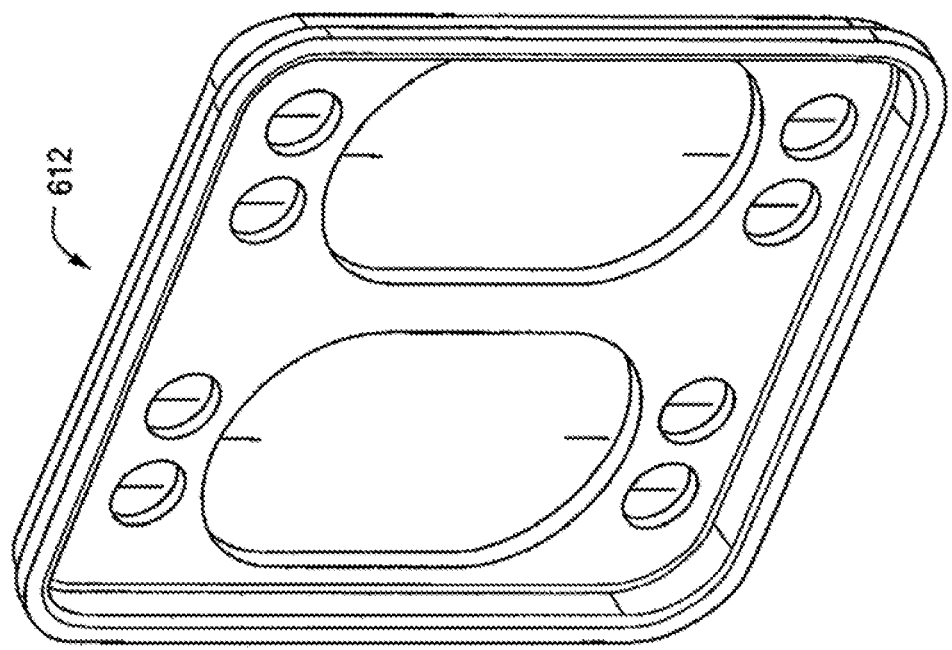
FIG. 3E shows a rear view of an exemplary bezel gasket in accordance with an embodiment of the present invention.
Figure 3D:
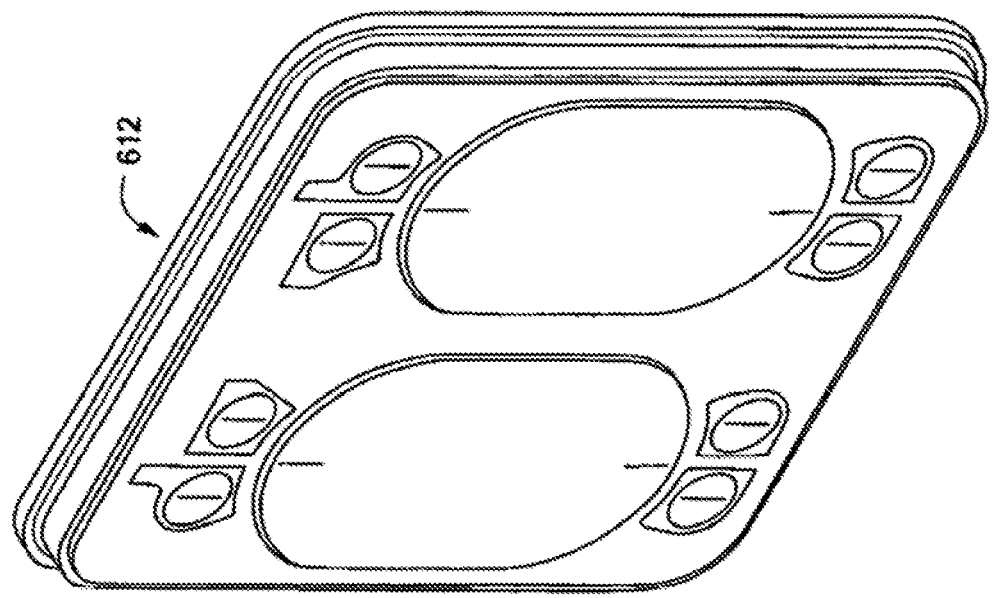
FIG. 3D shows a front view of an exemplary bezel gasket in accordance with an embodiment of the present invention.

FIG. 3D shows a front view of an exemplary bezel gasket 612 in accordance with an embodiment of the present invention. The bezel gasket 612 fits over the front of the bezel 604 and acts as an interface between the bezel 604 and the pump cassette 202 for sealing the fluid paths of the pump cassette 202 and for actuating the chambers and valves of the pump cassette 202. The pump cassette 202 is pressed firmly against the front side of the bezel gasket 612 during blood processing in order to produce an air-tight seal between the bezel gasket 612 and the pump cassette 202. For example, in various embodiments the bezel gasket 612 will properly seal against the pump cassette 202 when pressed together at a pressure of 7.5 to 8.0 psig. The bezel gasket 612 includes membranes that correspond to the chamber cavities and valve cavities. Positive and negative air pressure produced through the bezel cavities (typically, without limitation, at a pumping pressure of approximately −3.8 to 3.8 psig) operate on the bezel gasket membranes, which in turn operate on the chambers and valves of the pump cassette 202.

FIG. 3E shows a rear view of an exemplary bezel gasket 612 in accordance with an embodiment of the present invention. The rear side of the bezel gasket 612 contacts the front side of the bezel 604, and is pressed firmly against the bezel 604 during operation in order to produce an air-tight seal. The bezel gasket 612 includes membranes that correspond to the chamber cavities and valve cavities. Positive and negative air pressure produced through the bezel cavities operate on the bezel gasket membranes, which in turn operate on the chambers and valves of the pump cassette 202.

Referring back to FIG. 1, the process continues by inserting the pump cassette into a cassette receptacle, in block 2006. The cassette receptacle typically includes a support into which the pump cassette 202 may be slid or otherwise placed into. The support may include a latch to secure the pump cassette 202 in the cassette receptacle.

After inserting the pump cassette into the cassette receptacle, a movable member is moved against at least one of the cassette receptacle and the pump cassette 202 to press the pump cassette 202 against the control assembly 408, in block 2008. Advantageously pressing the pump cassette 202 against the control assembly 408, as opposed to pressing the control assembly 408 against the pump cassette 202, results in fewer tolerance accumulations, since the control assembly is typically coupled to a larger number of components that would apply various forces on the control assembly. The force applied by the movable member on the pump cassette 202 ensures a proper seal between the pump cassette 202 and the control assembly 408.

The movable member may be an expandable member, such as a bladder. Among other things, the bladder may be made from an elastic, resilient, and/or flexible material(s). A pneumatic circuit may be precisely controlled to inflate the expandable member with a predetermined amount of air. The predetermined amount of air may be programmable based on characteristics of the particular pump cassette 202. In other exemplary embodiments, the moving member may be a rigid structure whose movement is controlled by, for example, a motor.

The movable member may be attached to a door assembly that allows access to the cassette receptacle, such that the cassette pump 202 can be loaded and/or aligned. The door assembly may also help to prevent accidental opening of the door during blood processing, as described in more detail below.

Figure 4A:
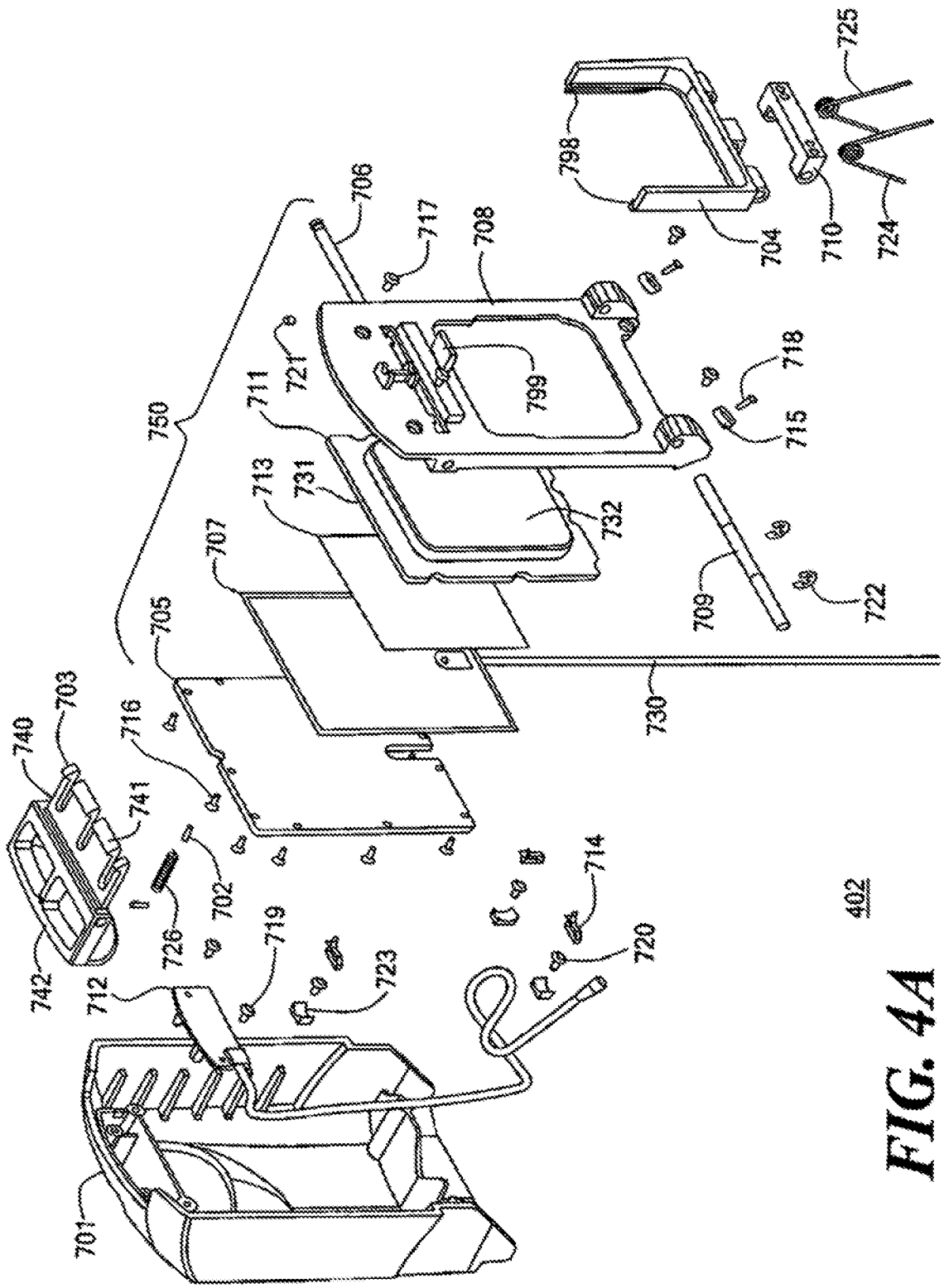
FIG. 4A shows an exploded view of a door assembly in accordance with an embodiment of the present invention.

FIG. 4A shows an exploded view of a door assembly 402 in accordance with an embodiment of the present invention. Among other things, the door assembly 402 may include a door cowl 701, a latch spring post 702, a door latch 703 (including handle 742, post 740, and projection 741), a cassette receptacle 704, a back plate 705, a latch pin 706, a bladder 707 with an attached pneumatic circuit 730, a piston assembly 711 including a a piston plate 731 and a piston cover 732, double coated tape 713, a frame 708, a door pin 709, a door mounting bracket 710, a human interface board assembly 712, a miniature cable tie 714, recessed bumpers 715, E-rings 722, cable tie mount 723, torsion springs 724 and 725, extension spring 726, a cassette orientation tab 799, and various screws 716, 717, 718, 719, 720, and 721. The human interface board assembly 712 is mounted to the inside of the door cowl 701.

As shown in FIG. 4A, the bladder 707 may be coupled to a piston assembly 711 that provides a surface for making contact with the pump cassette 202 and/or cassette receptacle 704. Among other things, using the piston assembly 711 advantageously reduces wear on the bladder 707. The piston assembly 711 may attach to the bladder 707 using, without limitation, various adhesives in the art, such as glue and/or tape 713, which may be double-sided tape. The piston assembly 711 includes a rigid plate 731 made of for example, a hard plastic. The piston plate 731 includes a protrusion that is covered by the piston cover 732. The piston cover 732 may be made of, without limitation, an elastomer. The protrusion of the piston plate 731 is designed to fit through an opening in the frame 708 so as to move back and forth through the opening when the bladder 707 is alternately inflated and deflated, as discussed below.

For support, the piston assembly 711 and bladder 707 are sandwiched between a rigid back plate 705 and the frame 708, which are mechanically coupled together to form a frame assembly 750. The frame assembly 750 is mounted to the inside of the door cowl 701 so that the door latch 703 protrudes through the frame assembly 750 and the frame assembly 750 holds the door latch 703 in place via latch pin 706. In other embodiments of the present invention, the frame assembly 750 can be mounted to the assembly 104.

The bladder 707 is coupled to, and controlled by, a pneumatic circuit 730 that provides positive and/or negative air pressure to the bladder 707. Positive pressure supplied to the bladder 707 causes the bladder 707 to expand in the direction of the frame 708. This, in turn, causes the entire piston assembly 711 to move toward the control assembly 408, such that the piston cover 732 presses against the pump cassette 202 and/or cassette receptacle 704, thereby producing an outward force on the door 402 away from the control assembly 408. Alternatively, supplying negative pressure to the bladder 707 causes the piston assembly 711 to move away from the pump cassette 202 and/or cassette receptacle 704, thereby reducing the outward force on the door 402 away from the control assembly 408.

The frame assembly 750 is further mounted to the inside of the door cowl 701 via screws 717. So as to allow easy access to the pump cassette 202, the cassette receptacle 704 is pivotally mounted (or otherwise movably mounted) to the frame 708 using the door mounting bracket 710, the door pin 709, and the E-rings 722. The cassette receptacle 704 is typically mounted so that the door rotates or otherwise moves the cassette receptacle 704 away from the bezel assembly (described above) when the door 402 is opened. Among other things, this causes the pump cassette to separate from the bezel gasket (described above) when the door 402 is opened, making it easier to remove and insert cassettes. In various embodiments, the cassette receptacle may only or further be mounted to the pump control assembly 408 or a location elsewhere on the pumping apparatus. The cassette receptacle 704 is typically oriented such that the pump cassette is dropped into the cassette receptacle 704 from the top, although the cassette receptacle 704 can be oriented in other ways, for example, such that the pump cassette is slid into the cassette receptacle 704 from the side.

When the pump cassette 202 is inserted into the cassette receptacle 704, the bottom portion of the peripheral rib 303 rests on the bottom of the cassette receptacle 704 so that the membrane portion of the cassette receptacle 704 is raised above the bottom of the cassette receptacle 704. Also, the cassette receptacle 704 includes cassette containment brackets 798 on the side of the cassette receptacle 704 facing the door. The cassette containment brackets 798 engage the side portions of the peripheral rib 303 when the door is closed in order to secure the pump cassette 202 without contacting the membrane on the pump cassette 202. Among other things, the peripheral rib 303 allows the pump cassette 202 to be seated in the cassette receptacle 704 while leaving the entire surface of the pump cassette membrane exposed for contact with the piston cover 732. There are preferably no cassette containment brackets on the side of the cassette receptacle 704 facing away from the door, which, among other things, facilitates insertion and removal of the pump cassette 202, as the pump cassette 202 is not required to be inserted within a slot or channel such as would be formed by opposing brackets. The cassette orientation tab 799 prevents the door from being closed if the pump cassette is oriented incorrectly in the cassette receptacle 704, and also makes contact with the top rib 301 of the pump cassette 202 in order to limit vertical travel of the pump cassette 202.

The door latch 703 is positioned so that a handle portion is accessible from a front side of the door cowl 701. The frame assembly is mounted to the inside of the door cowl 701 so that a latch portion of the door latch 703 protrudes through the frame assembly and the frame assembly holds the door latch 703 in place. The torsion springs 724 and 725 aid the operator in closing the door, as the door has considerable weight due to the many components. Recessed bumpers 715 can be used to reduce strain on the door if the door is opened too far or with excessive force.

The door assembly may be designed to permit single-handed operation, such as by pulling up on the handle. However, the door latch 703 is designed so that the door cannot be easily opened when the pump cassette 202 is in place in the cassette receptacle 704 with the door closed and the piston assembly 711 is inflated. Specifically, the latch portions of the door latch 703 have undercuts that are engaged by recesses in the control assembly 408. When the pump cassette is in place in the cassette receptacle 704 with the door closed and the piston assembly 711 is inflated so as to push the pump cassette 202 against the bezel assembly of the control assembly 408, a sufficient force is generated between the door assembly 402 and the control assembly 408 to prevent the door handle from being easily lifted. This door locking mechanism is described in greater detail in Application D74.

Figure 4B:
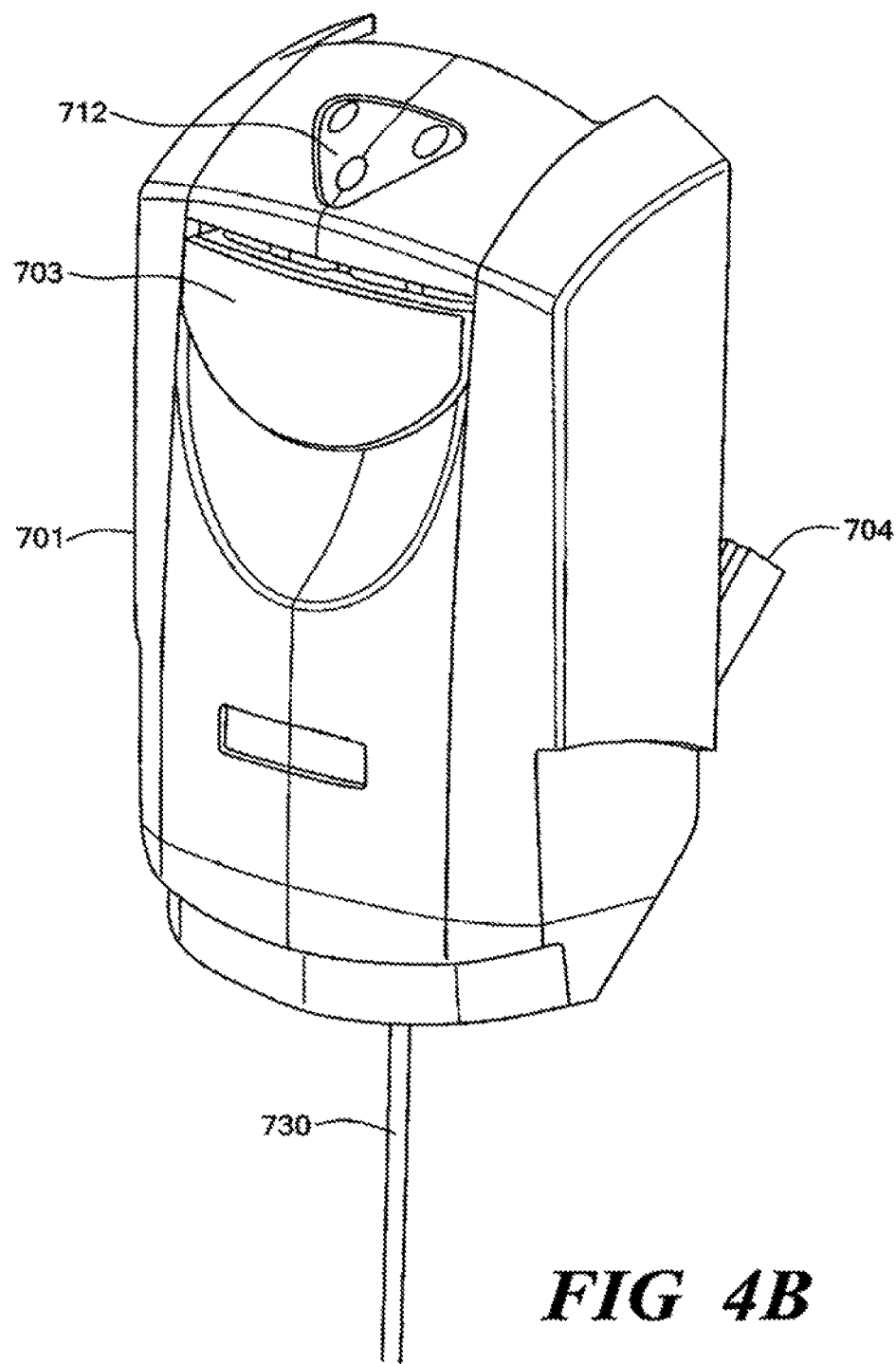
FIG. 4B shows a front perspective view of the door assembly in accordance with an embodiment of the present invention.

FIG. 4B shows a front perspective view of the door assembly 402 in accordance with an embodiment of the present invention. The human interface board assembly 712 having LEDs or other operator controls, and the handle portion of the door latch 703, are visible from the front of the door cowl 701. A portion of the cassette receptacle 704 is also visible.

Figure 4C:
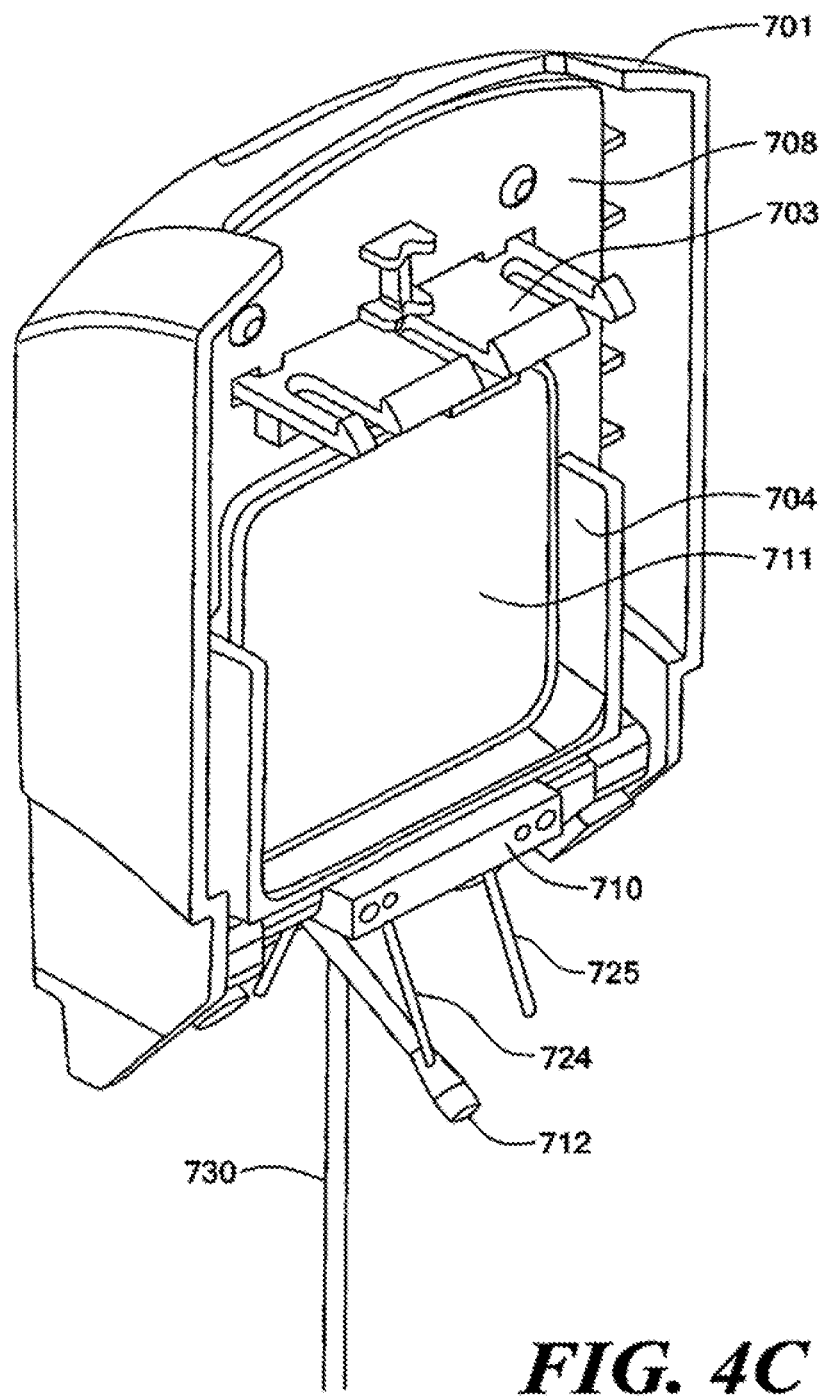
FIG. 4C shows a rear perspective view of the door assembly in accordance with an embodiment of the present invention, in which the cassette receptacle is in a retracted position.

FIG. 4C shows a rear perspective view of the door assembly 402 in accordance with an embodiment of the present invention, in which the cassette receptacle 704 is in a retracted position. Visible at the rear of the door cowl 701 are the frame 708, the latch portion of the door latch 703, the cassette receptacle 704, the piston assembly 711, the door mounting bracket 710, the torsion springs 724 and 725, and a portion of the human interface board assembly 712.

Figure 4D:
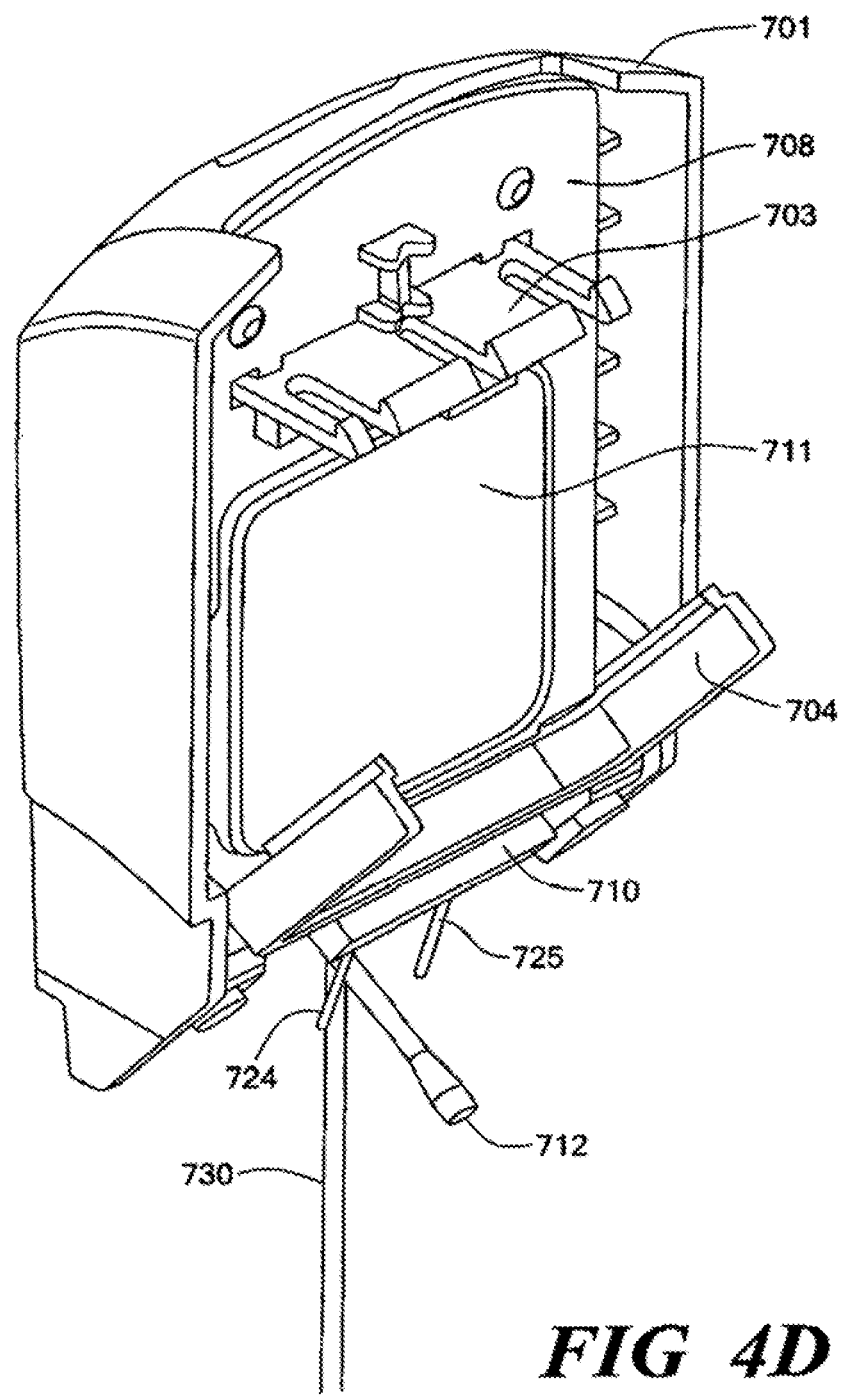
FIG. 4D shows a rear perspective view of the door assembly in accordance with an embodiment of the present invention, in which the cassette receptacle is in an open position.

FIG. 4D shows a rear perspective view of the door assembly 402 in accordance with an embodiment of the present invention, in which the cassette receptacle 704 is in an open position. Visible at the rear of the door cowl 701 are the frame 708, the latch portion of the door latch 703, the cassette receptacle 704, the piston assembly 711, the door mounting bracket 710, the torsion springs 724 and 725, and a portion of the human interface board assembly 712.

In certain embodiments of the present invention, the cassette tends to stick to the bezel gasket and/or the door piston after the door piston is inflated to seal the cassette against the bezel gasket. Therefore, a door assembly may include a positive release mechanism that pulls the cassette away from both the bezel gasket and the door piston when the door is opened so as to release the cassette for removal.

FIG. 4E shows an exemplary door assembly 760 including a positive release mechanism in accordance with an alternate embodiment of the present invention. Among other things, the door assembly 760 includes a door 762 pivotably mounted to a mounting bracket 772 of a front plate assembly 761 via a hinge 771. The door assembly 760 also includes a cassette receptacle 764 pivotably mounted to a support 763, which itself is pivotably mounted to the front plate assembly 761 and to the door 762. Each side of the support 763 includes a pin 770 that is engaged by a corresponding slot 769 in the door 762. The offset between the hinge 771 and the slot 769 causes the bottom of the support 763 to be pulled away from the front plate assembly 761 when the door 762 is pulled open and causes the bottom of the support 763 to be pushed toward the front plate assembly 761 when the door 762 is pushed closed. The cassette receptacle 764 is mounted to the support 763 in such a way that the cassette receptacle 764 is pulled away from the bezel gasket and away from the door piston when the door 762 is opened. In this way, the positive release mechanism pulls the cassette away from both the bezel gasket and the door piston when the door is opened so as to release the cassette for removal.

The cassette receptacle 764 of the door assembly 760 includes cassette containment brackets for supporting both sides of the cassette. Specifically, the cassette receptacle 764 includes a first pair of brackets 765 and 766 on one end and a second pair of brackets 767 and 768 at the other end. The brackets essentially form a slot or channel into which the cassette must be placed. In this embodiment of the invention, the cassette receptacle 764 is designed for use with a cassette lacking a peripheral rib, and the brackets 765-768 contact a portion of the membranes of the cassette.

The system described above may be used in a wide variety of applications. In exemplary embodiments of the present invention, an anti-pathogen solution can be mixed with a red blood cell concentrate (RBCC) to form an incubation solution for reducing pathogens in the RBCC. The anti-pathogen solution is prepared by mixing a caustic anti-pathogen compound (e.g., PEN110™ or INACTINE™), which is an organic solvent with a pH over 11 that is distributed by V.I. Technologies, Inc. of Watertown, Mass.) with a buffer solution of sodium phosphate to a predetermined concentration (e.g., 1 part anti-pathogen compound to 99 parts buffer solution), preferably as described in Application D70, which is hereby incorporated herein by reference in its entirety. For convenience, this mixing of anti-pathogen compound with buffer solution may be referred to hereinafter as "compounding," and an apparatus that performs such compounding may be referred to hereinafter as a "compounder" or "compounder pump." The incubation solution is prepared by mixing the anti-pathogen solution with the RBCC to a predetermined concentration (e.g., 1 part anti-pathogen solution to 9 parts RBCC), as described below. For convenience, this mixing of anti-pathogen solution with RBCC may be referred to hereinafter as "blood processing," and an apparatus that performs such blood processing may be referred to hereinafter as a "blood pump." Details of an blood processing system incorporating the illustrative pump apparatus flow below.

System Overview

Figure 5A:
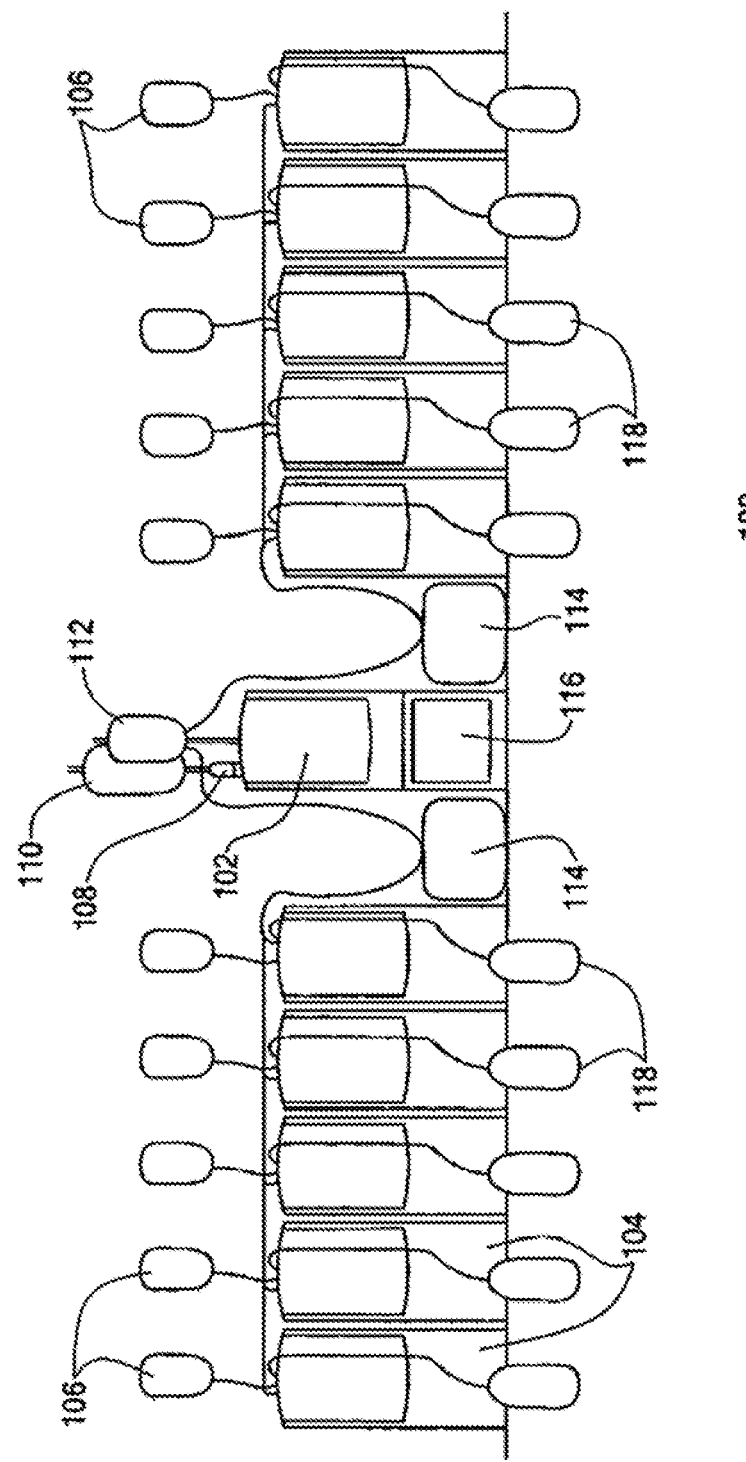
FIG. 5A shows an exemplary blood processing system having a plurality of blood pumps in accordance with an embodiment of the present invention.

FIG. 5A shows an exemplary blood processing system 100 having a plurality of blood pumps in accordance with an embodiment of the present invention. Among other things, the blood processing system 100 includes a single compounder pump 102 and ten essentially identical blood pumps 104 organized as two banks of five blood pumps each. The compounder pump 102 pumps buffer solution from a buffer solution container 110 into a vial of anti-pathogen compound 108. The mixture, referred to as a working solution, is pumped into a working solution container 112. Each of the blood pumps 104 mixes working solution from the working solution container 112 with red blood cell concentrate (RBCC) from a RBCC container 106 to form an incubation solution that is pumped into an incubation bag 118. The incubation solution is typically allowed to incubate for some period of time, after which it is rinsed to remove the anti-pathogen compound to produce a pathogen reduced blood product. The blood processing system 100 typically also includes two sterile docks 114 that are used by the operator to splice together plastic tubing as necessary for various blood processing operations. The blood processing system 100 is controlled through a user interface 116.

Figure 5B:
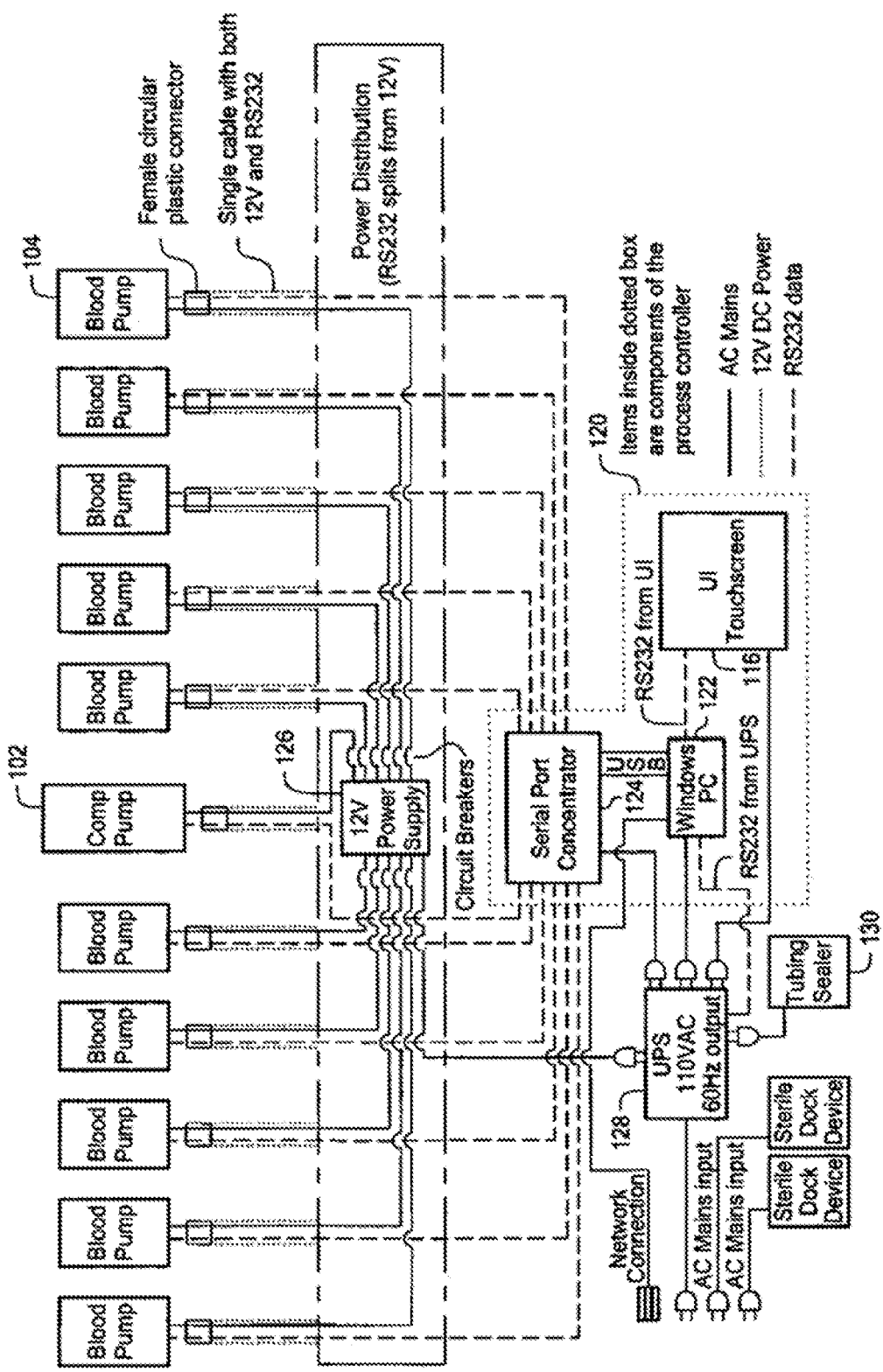
FIG. 5B shows an exemplary wiring diagram for one embodiment of the blood processing system shown in FIG. 5A.

FIG. 5B shows an exemplary wiring diagram for one embodiment of the blood processing system 100. The compounder pump 102 and the blood pumps 104 are typically powered from a common 12-Volt external power supply 126, and are controlled by an external process controller 120. The process controller 120 includes the user interface 116, a computer 122, and a serial port concentrator 124. The compounder pump 102 and the blood pumps 104 are in communication with the process controller 120 through the serial port concentrator 124, for example, over RS-232 communication links. The blood processing system 100 typically includes a tubing sealer 130 for sealing plastic tubing as necessary for various blood processing operations. The blood processing system 100 typically includes an uninterruptible power supply (UPS) 128 for maintaining electrical power to the 12-Volt power supply, the process controller, and other components in the event of a primary power loss.

Figure 5C:
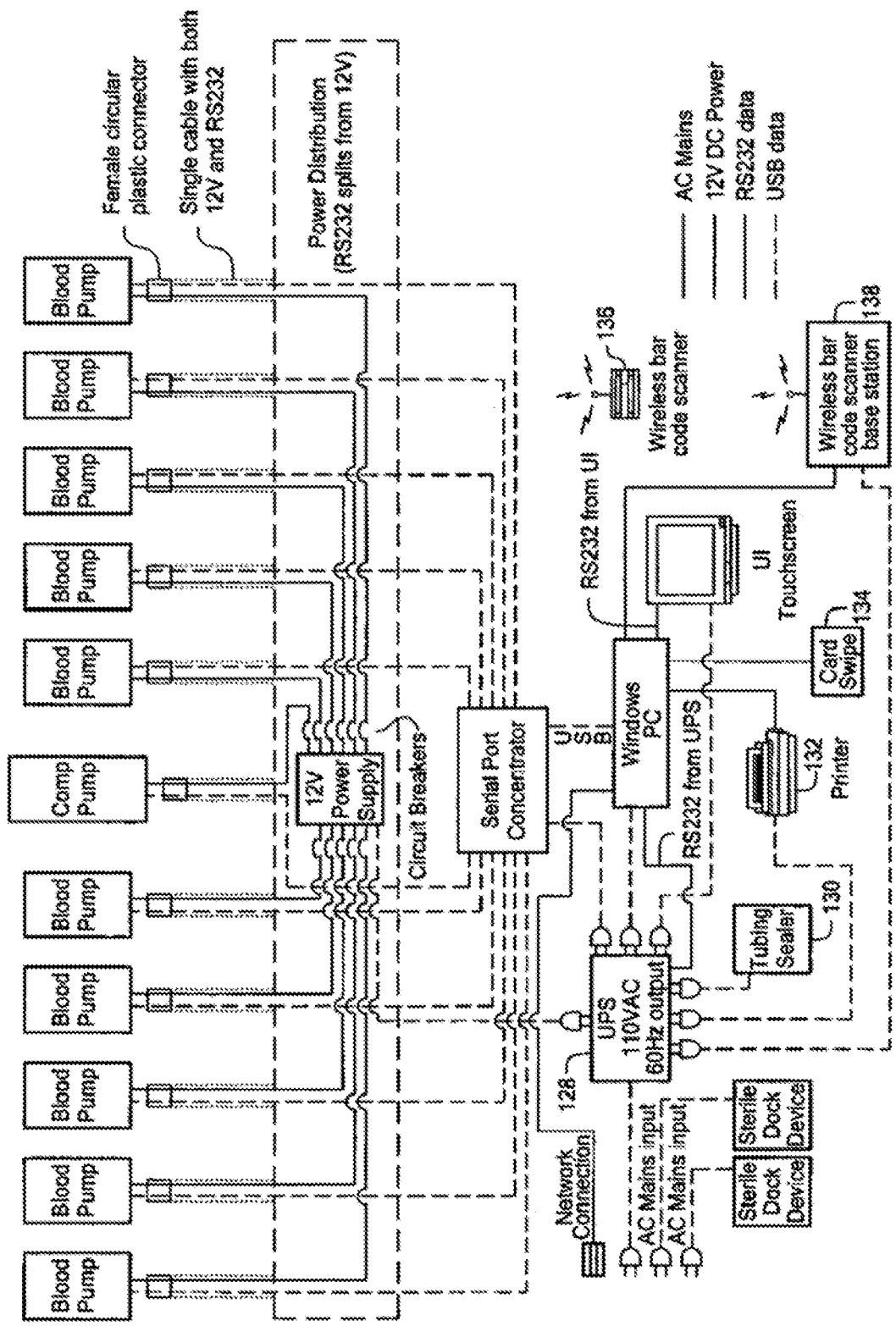
FIG. 5C shows an exemplary wiring diagram for another embodiment of the blood processing system shown in FIG. 5A.

FIG. 5C shows an exemplary wiring diagram for another embodiment of the blood processing system 100. The blood processing system 100 may include a printer 132 in communication with the process controller for printing out reports. The blood processing system 100 may include a card reader 134 in communication with the process controller for card-based operator identification. The blood processing system 100 may include a wireless bar code scanner base station 138 in communication with the process controller for receiving bar code information scanned using a wireless bar code scanner 136. Bar codes are typically used to track the various solution containers and the pumps on which those containers were processed.

The process controller 120 coordinates the actions of the compounder pump 102, the blood pumps 104, and the operator throughout the various mixing operations, as described in greater detail in Application D72. The process controller 120 initiates high level embedded commands within the pumps to move and mix the fluids. The process controller 120 instructs the operator through the setup and teardown of each process through the user interface 116. The user interface 116 is also used to inform the operator of any anomalies that may occur during mixing operations.

When the blood processing system 100 is operating from the uninterruptible power supply 128 and at other appropriate times, the process controller 120 will prevent compounding and other pump operations from starting, although the pumps will generally be allowed to complete any ongoing operations. Furthermore, if the process controller fails, the pumps have internal logic for safely completing or terminating any ongoing operations.

Blood Disposables

In an exemplary embodiment of the present invention, the process controller 120 coordinates blood processing for an entire bank of five blood pumps 104 at a time. Specifically, five pump cassettes, each connected to a RBCC container and an incubation bag for receiving the incubation solution, are loaded respectively into the five blood pumps 104. The five pump cassettes are preferably connected by a single working solution inlet tube to the working solution container so that all five blood pumps draw working solution from the single working solution container. For convenience, the five interconnected pump cassettes along with their respective incubation bags and various plastic tubing may be referred to hereinafter as a "blood disposables set." The blood disposables set is preferably used for a single blood processing cycle and is then discarded. The blood disposables set is described in greater detail in Application D85.

Figure 6:
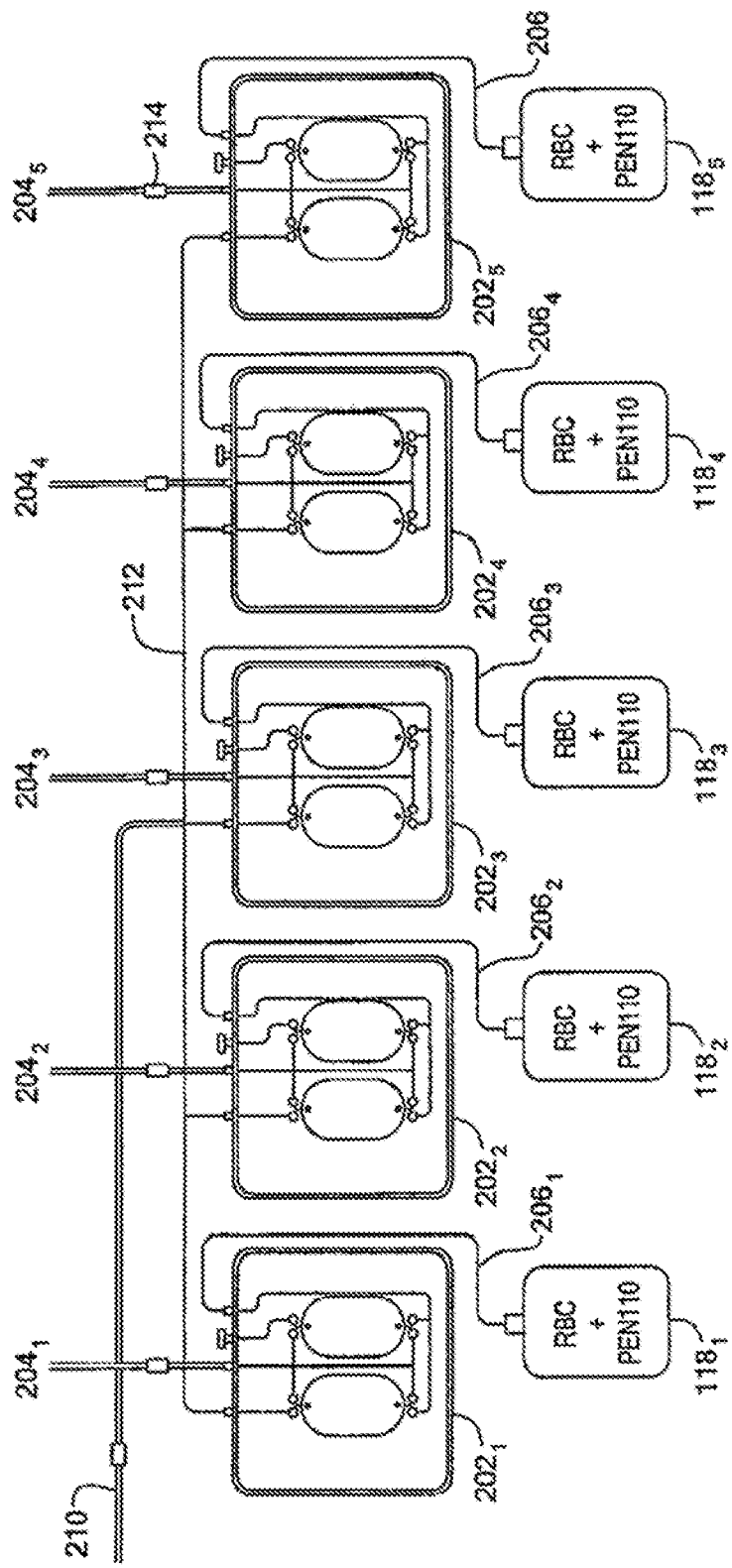
FIG. 6 shows an exemplary blood disposables set in accordance with an embodiment of the present invention.

FIG. 6 shows an exemplary blood disposables set 200 in accordance with an embodiment of the present invention. The blood disposables set 200 includes five pump cassettes 202.sub.1-5 which operate in accordance with above-described embodiments, each respectively having a RBCC inlet tube 204.sub.1-5 connected to an RBC inlet port of the pump cassette and an incubation solution outlet tube 206.sub.1-5 connected to an outlet port of the pump cassette and to an incubation bag 118.sub.1-5. The blood disposables set 200 also includes working solution distribution tubing 212 that connects to a working solution inlet port on each pump cassette 202.sub.1-5 and to a single working solution inlet tube 210 so that the working solution inlet ports of all pump cassettes 202.sub.1-5 are effectively connected to the single working solution inlet tube 210. The working solution inlet tube 210 preferably connects to the working solution distribution tubing 212 close to where the working solution inlet port of the middle pump cassette 202.sub.3 connects to the tubing 212, and the working solution inlet ports of each concentric pair of pump cassettes is preferably connected to the tubing 212 a substantially equal distance from that center connection such that the working solution inlet ports of the pump cassettes 202.sub.1 and 202.sub.5 are essentially equidistant from the center connection and the working solution inlet ports of the pump cassettes 202.sub.2 and 202.sub.4 are essentially equidistant from the center connection. Among other things, this spacing of pump cassettes along the tubing 212 facilitates priming of the pumps, as discussed below. In order to perform blood processing, each RBCC inlet tube 204 is connected to a separate RBCC container 106, and the working solution inlet tube 210 is connected to the common working solution container 112. The blood disposables set 200 also includes six break-away closures 214, one on each of the RBCC inlet tubes 204 and one on the working solution inlet tube 210. In order to reduce the likelihood of confusing which RBCC bag and which incubation bag is associated with each pump cassette, the RBCC inlet tubes 204 and the incubation solution outlet tubes 206 are preferably coded, for example, by alternating between color-striped and clear tubing from cassette to cassette.

Referring back to FIGS. 2(a) and 2(b), each pump cassette 202 includes, among other things, a working solution inlet port 304, an RBC inlet port 305, a vent port 307, an outlet port 308 and two pumping chambers, namely a working solution chamber 333 and an RBC chamber 334. During blood processing, working solution from the working solution container 112 is drawn into the working solution chamber 333 through the tubing 210 and 212 and the working solution inlet port 304, and is pumped from the working solution chamber 333 into the channel 310 while RBCC from the RBCC container 106 is drawn into the RBC chamber 334 through the RBCC inlet tube 204, the RBCC inlet port 305, and the channel 310. This causes the working solution and RBCC to be mixed within the channel 310 and the RBC chamber 334. The mixture (incubation solution) is pumped from the RBC chamber 334 to the incubation bag 118 through the outlet port 308 and the incubation solution outlet tube 206.

Pump cassette 202 also includes a RBC priming valve 326, an RBC valve 328, an incubation bag valve 330, a working solution valve 332, and a working solution connection to RBC line valve 336. These valves and the pumping chambers are all operated pneumatically from the rear of the pump cassette 202.

Blood Pump

As discussed above, each blood pump 104 prepares incubation solution by mixing an anti-pathogen solution with RBCC. A disposable pump cassette 202 is used to handle the various fluids. The pump cassette 202 serves as an interface between the blood pump 104, the RBCC container 106, and the incubation bag 118 so that no working solution, RBCC, or incubation solution comes into actual contact with the components of the blood pump 104. The blood pump 104 preferably uses pneumatics to operate the pump cassette 202 as well as other components, as discussed below.

The blood pump 104 produces the incubation solution by causing working solution to be drawn into the working solution chamber 333 and pumping working solution from the working solution chamber 333 into the channel 310 while drawing RBCC into the RBC chamber 334 through the channel 310. This causes the working solution and RBCC to be mixed within the channel 310 and the RBC chamber 334. The mixture (incubation solution) is pumped from the RBC chamber 334 to the incubation bag 118 through the outlet port 308.

In a typical embodiment of the present invention, the working solution is pumped from the working solution chamber 333 using a pulsing technique in which small quantities of working solution are pumped at predetermined intervals and the pulsing of working solution is adjusted periodically using a closed feedback loop in order to produce an incubation solution having a predetermined concentration of working solution, with predetermined limits. Specifically, the working solution is delivered in a pulsatile mode where the pulse width of the exit valve on the working solution chamber is controlled. The fluid valve is pulsed at a pulse width and interval that is predetermined for each pumping stroke and is adjusted stroke-by-stroke according to the amounts of working solution and RBCC pumped, as described below. The blood pump 104 can support pulse widths above some minimum value, and the interval between pulses is increased in order to achieve an effective pulse width below the minimum value.

The blood pump 104 preferably includes a library of generic pump control (N-Pump) functions. The N-Pump library functions are used to perform various generic pumping operations such as, for example, pumping fluid into a chamber of the pump cassette, pumping fluid out of a chamber of the pump cassette, measuring the amount of fluid pumped, performing air detection, and maintaining tank pressures. The blood pump 104 preferably also includes a Fluid Logic Module (FLM) that contains higher level functions that employ the N-Pump library functions to implement application-specific functions (such as specific logic for mixing the working solution with the RBCC to produce the incubation solution).

The blood pump 104 includes one master board connected to two pump boards that together perform the N-Pump and FLM functions. The master board communicates to each of the pump boards via a multi-drop RS-485 bus. Each pump board controls a single pump chamber of the pump cassette 202 and the valves on its board.

Figure 7:
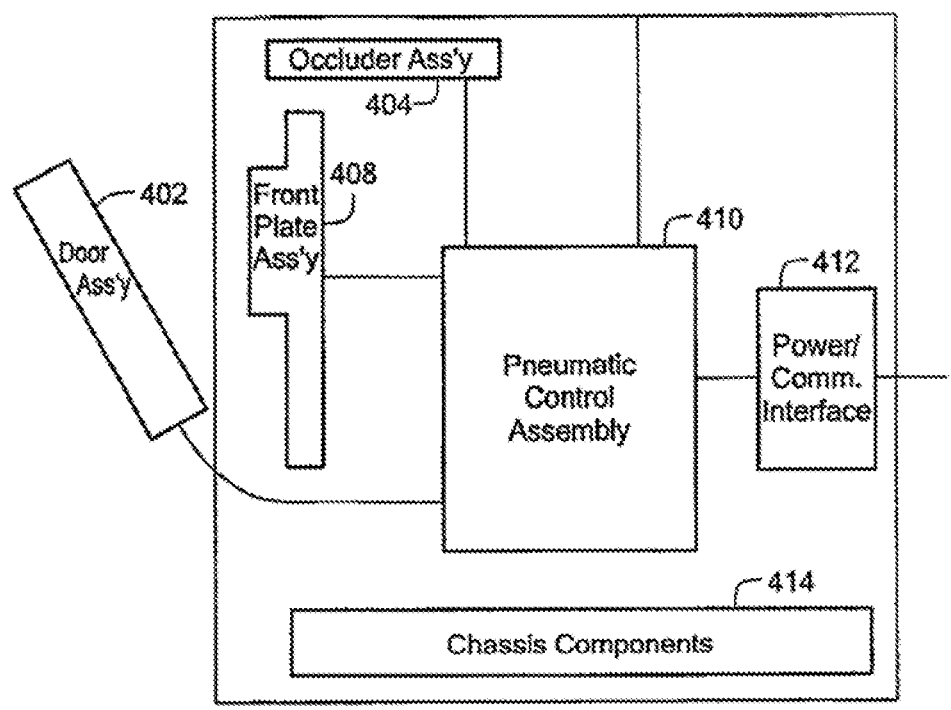
FIG. 7 shows a conceptual block diagram of the blood pump in accordance with an embodiment of the present invention.

FIG. 7 shows a conceptual block diagram of the blood pump 104 in accordance with an embodiment of the present invention. Among other things, the blood pump 104 includes the door assembly 402 as described in above embodiments of the invention, an occluder assembly 404, the control assembly 408 as described in above embodiments of the invention, a pneumatic control assembly 410, a power/communication interface 412 including connectors for the 12-Volt power supply and the RS-232 communication link to the process controller 120, and chassis components 414. Each of these assemblies is discussed below.

Pneumatic Control Assembly

The pneumatic control assembly 410 provides positive and negative air pressure for operating the various other pneumatically controlled components and also acts as the general controller for the blood pump 104.

The pneumatic control assembly 410 contains three electromechanical pump module assemblies, namely a tank management module assembly and two chamber module assemblies (one for the working solution pump chamber and one for the RBC pump chamber). Each pump module assembly includes an aluminum manifold, pneumatic valves, pneumatic fittings, a valve interface board, and an electronics board that includes pressure transducers and a dedicated microprocessor. The tank management module assembly handles all communication between the blood pump and the process controller 120, synchronizes pumping of the chamber module assemblies, maintains positive and negative air pressure in various accumulators, seals and unseals the door assembly, engages and disengages the occluders, monitors the door open/closed status, and monitors the air-in-line sensor, as described below. Each chamber management assembly controls a separate one of the pump chambers, and also controls the fluid valves associated with the pump chamber and measures the volume of liquids pumped through the pump chamber.

Figure 8A:
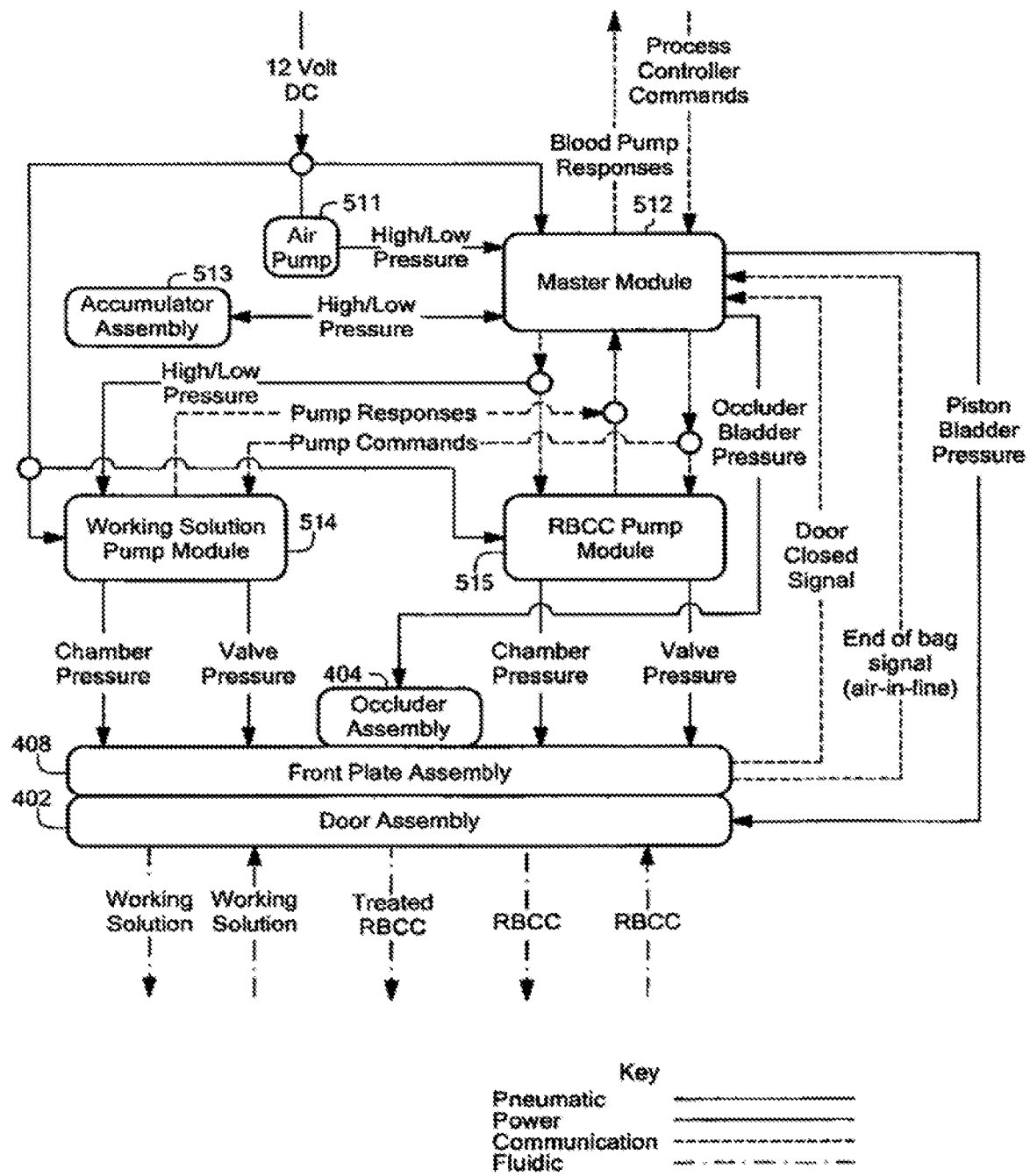
FIG. 8A is an architectural flow diagram showing the relationship between the pneumatic control assembly and the other assemblies in accordance with an embodiment of the present invention.

FIG. 8A is an architectural flow diagram showing the relationship between the pneumatic control assembly 410 and the other assemblies in accordance with an embodiment of the present invention. In this figure, the pneumatic control assembly 410 is represented by master module 512, accumulator assembly 513, working solution pump module 514, and RBCC pump module 515. The air pump 511 is considered to be one of the chassis components 414. The air pump 511 generates high and low air pressure for the master module 512, which stores high and low air pressure in the accumulator assembly 513. The pneumatic control assembly 410 directs air pressure (positive and negative) to the various pneumatic mechanisms of the pump. The master module 512 pneumatically controls bladders in the occluder assembly 404 and the bladder in the door assembly 402. The master module 512 provides high and low air pressure to the working solution pump module 514 and the RBCC pump module 515. The working solution pump module 514 controls the working solution chamber 333 and associated valves of the pump cassette 202 through the control assembly 408, and the RBCC pump module 515 controls the RBC chamber 334 and associated valves of the pump cassette 202 through the control assembly 408.

Figure 8B:
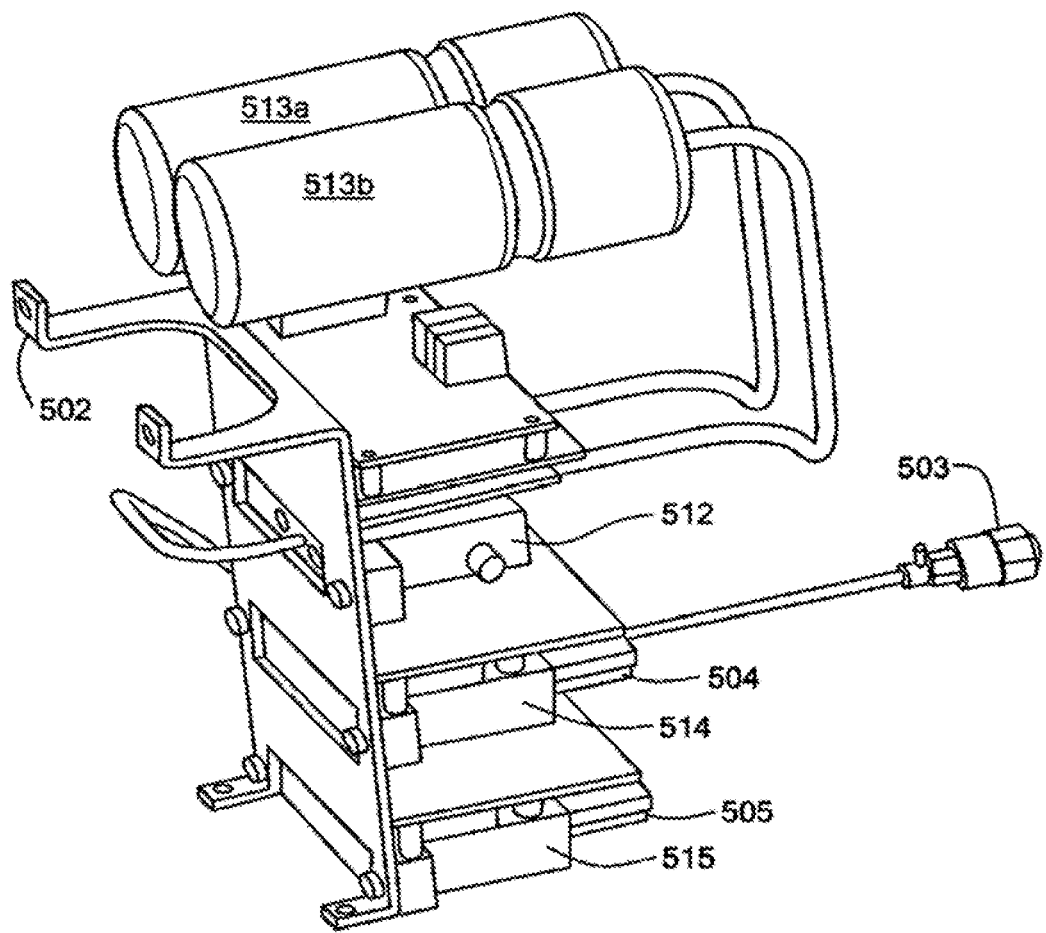
FIG. 8B shows an exemplary embodiment of the pneumatic control assembly in accordance with an embodiment of the present invention.

FIG. 8B shows an exemplary embodiment of the pneumatic control assembly 410 in accordance with an embodiment of the present invention. Among other things, the pneumatic control assembly 410 includes manifold mounting bracket 502, a negative pressure accumulator (pressure bottle) 513a, a positive pressure accumulator (pressure bottle) 513b, a manual door vent mechanism 503, the Tank Management Module Assembly 512, the two Chamber Module Assemblies 514 and 515, and associated tubing and fittings.

The tank management module 512 includes an input/output (I/O) board, a CPU board, a valve-interface board, a pneumatic manifold system, pneumatic valves, pressure transducers 2-vent covers (mufflers), stand-offs, and associated tubing and fittings. The tank management module 512 is used to control the pressures in the accumulators 513, the bladder in the door assembly 402, and bladders in the occluder assembly 404. The I/O board contains electrical controls for controlling LEDs that provide status information to the operator. The pressure transducers are used to monitor the pressures of the accumulators 513 and the bladder in the door assembly 402.

In the un-powered state, the pneumatic valve that controls flow to the bladder in the door assembly 402 preferably shuts closed. This prevents the door from being opened in the event of a loss of power.

In the un-powered state, the pneumatic valves that control flow to the bladders in the occluder assembly 404 are preferably channeled to vent. This causes the occluders to occlude the tubing to prevent further flow of fluid through the tubing, as discussed below.

Each chamber module 514 and 515 includes a CPU board, a valve interface board, pneumatic manifold system, pneumatic valves (including a VSO (variable) valve), a VSX chamber (504 and 505 respectively), O-ring, copper mesh, vent cover (muffler), stand-offs, pressure transducers, and associated tubing and fittings. Each chamber module assembly controls the pneumatics for one of the pumping chambers and its associated valves. The VSX chambers 504 and 505 act as reference volumes in order to measure the volume of fluid that is delivered with the FMS system. The pressure transducers are used to monitor the pressure of the VSX chamber, and of the pumping chamber. The positive pneumatic system contains a pressure relief valve to prevent the air pump from pressurizing the positive system to greater than 16.0 psig.

In the un-powered state, all of the pneumatic valves preferably open the fluid valves to the positive pressure line. This ensures that the fluid valves are closed if there is a loss of power.

The blood pump 104 typically includes three microprocessor systems, one on the tank management module 512 and one on each of the chamber modules 514 and 515. These three microprocessor systems monitor each other for normal operation. Each microprocessor system also monitors key internal processes and data for validity. If any of these monitors fail, a failsafe line permits any of the three processors to stop pumping operations, close all of the fluid valves and occluder, and send an anomaly signal to the process controller. If the blood pump 104 detects an anomaly with the commands received from the process controller (e.g., commands received out of sequence), then the blood pump 104 will stop fluid flow and send an anomaly signal to the process controller.

Control Assembly

The control assembly 408, described in above embodiments of the invention, is utilized in the following manner:

Referring back to FIGS. 3A-3D, the air-in-line sensor 610 is positioned so as to align with and engage the RBCC inlet tube 204. The air-in-line sensor is used during blood processing to detect air in the RBCC inlet tube 204 indicating that there is no more RBCC to be processed.

The bezel 604 defines, among other things, a working solution chamber cavity 633 for operating the working solution chamber 333 of the pump cassette 202, an RBC chamber cavity 634 for operating the RBC chamber 334 of the pump cassette 202, and various valve cavities 635 for operating the various valves of the pump cassette 202. The working solution chamber cavity 633 is molded with rib structures 636 that, as described above, allow for airflow within the working solution chamber cavity 633 but mechanically restrict the amount of working solution that can be drawn into the working solution chamber 333 of the pump cassette 202. The compounder 102 preferably uses the same molded bezel 604 as the blood pump 104, but with the rib structures 636 removed (e.g., by precision machining) to allow for greater pumping capacity.

Front Plate (Control) Assembly

The control assembly 408 is used as described above.

Occluder Assembly

The occluder assembly 404 mounts to the back of the control assembly 408, and is used to selectively occlude the RBCC inlet tube 204, the incubation solution outlet tube 206, and the working solution distribution tube 212 as needed for testing, blood processing, and protection in the event of a failure.

In the blood pump 104, the occluder assembly 404 includes two occluders, one operating on both the RBCC inlet tube 204 and the incubation solution outlet tube 206, and the other operating on the working solution distribution tube 212. The occluders are controlled pneumatically, and can be controlled independently.

In a typical embodiment of the present invention, each occluder includes an occluder blade that is operated by a flat spring and an inflatable bladder. The occluder blade is coupled to one end of the spring. When the bladder is deflated, the spring extends the occluder blade into an occluding position, which blocks the passage of fluid through the tube(s). When the bladder is inflated, the bladder bends the spring so as to retract the occluder blade from the occluding position, which enables the passage of fluid through the tube(s). In the event of a loss of pneumatics, the occluder defaults to the occluded position so as to prevent fluid from passing through the tubing.

Figure 9:
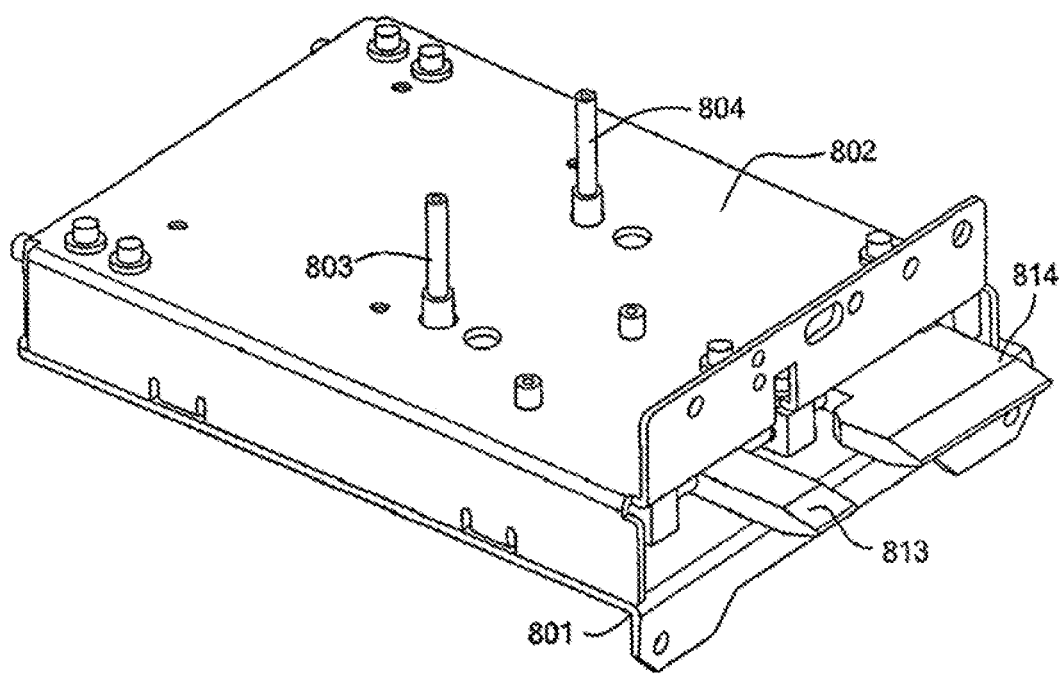
FIG. 9 shows a side perspective view of the occluder assembly in accordance with an embodiment of the present invention.

FIG. 9 shows a side perspective view of the occluder assembly 404 in accordance with an embodiment of the present invention. The occluder assembly 404 includes, among other things, a bottom housing 801, a top housing 802, a first occluder having an occluder blade 813 and other components operated pneumatically through tube 803, and a second occluder having an occluder blade 814 and other components operated pneumatically through tube 804. The occluder assembly 404 is mounted to the control assembly 408, with the occluder blades 813 and 814 protruding through slots in the control assembly 804. The tubes 803 and 804 are connected to the pneumatic control assembly 410.

Figure 10:
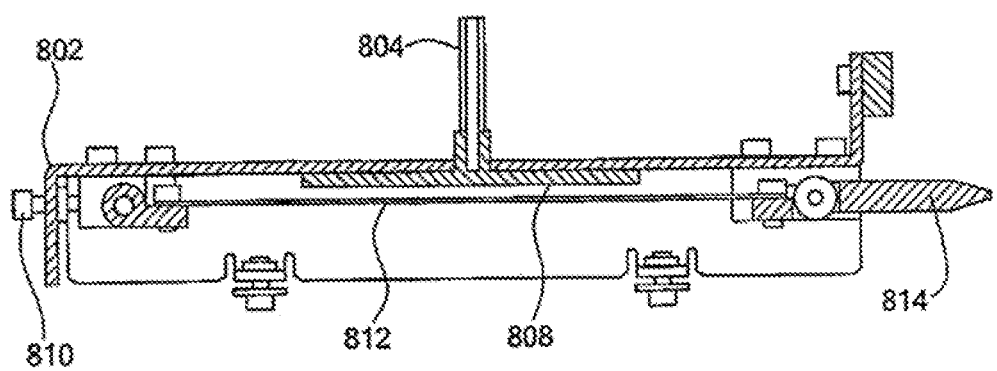
FIG. 10 shows a cross-sectional view of an occluder in accordance with an embodiment of the present invention.

FIG. 10 shows a cross-sectional view of an occluder assembly 404 in accordance with an embodiment of the present invention. Among other things, the occluder includes a flat occluder spring 812 having a rear end coupled to the top housing 802 and a front end coupled to the occluder blade 814, a bladder 808 situated between the top housing 802 and the spring 812, the tube 804 coupled to the bladder 808, and an adjuster 810 for adjusting the protrusion of the occluder blade 814. When the bladder 808 is inflated, the occluder spring 812 is deflected downward at the middle so as to shorten the effective length of the occluder spring 812 and retract the occluder blade 814. When the bladder 808 is deflated, the occluder spring 812 extends flat and therefore extends the occluder blade 814. The occluder blade 814 moves within guides (not shown) that allow the spring to extend and retract the occluder blade 814.

Figure 11:
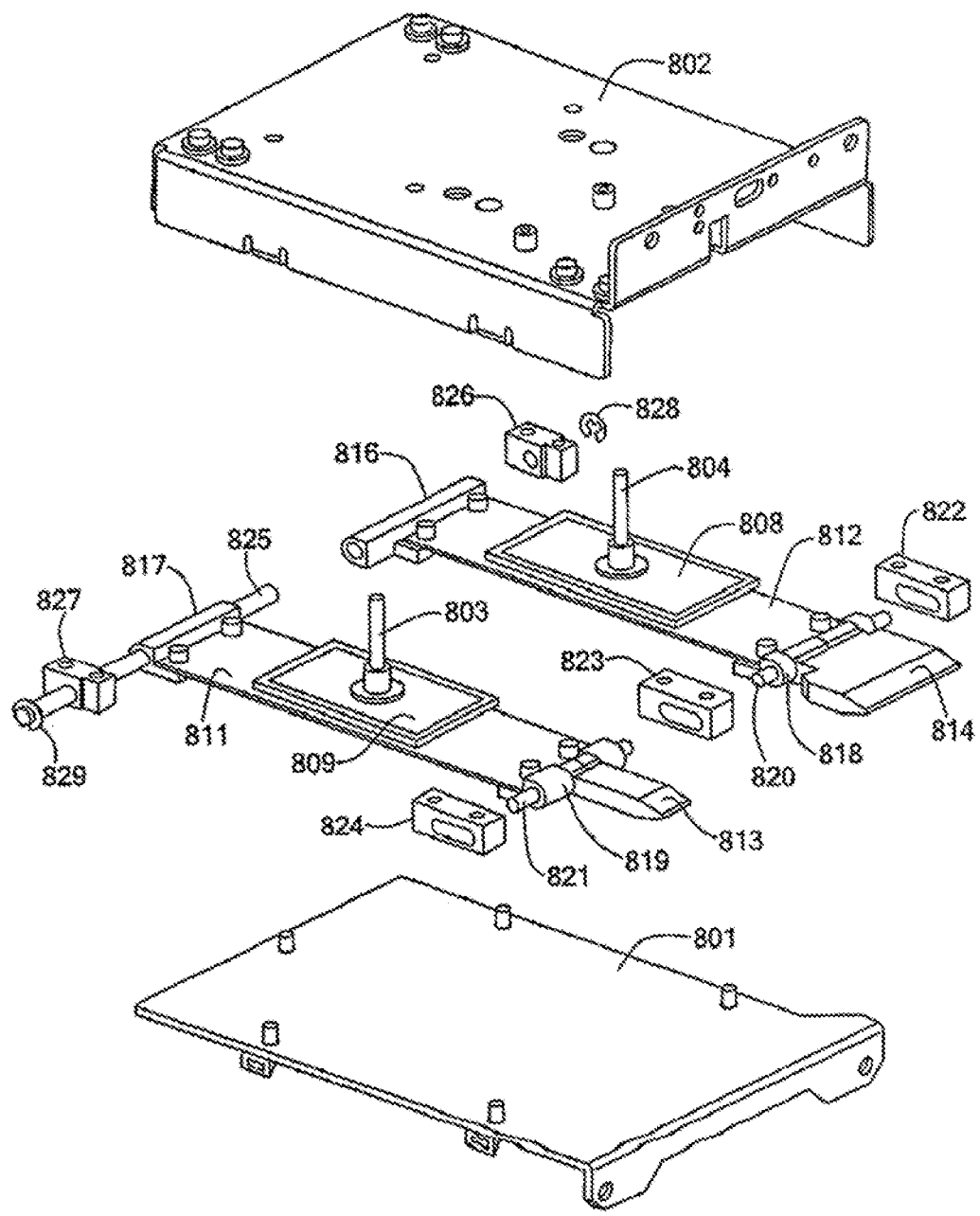
FIG. 11 shows an exploded view of the occluder assembly in accordance with an embodiment of the present invention.

FIG. 11 shows an exploded view of the occluder assembly 404 in accordance with an embodiment of the present invention. Among other things, the occluder assembly 404 includes enclosure top 802, enclosure bottom 801, a first occluder including a flat occluder spring 811 coupled to an occluder blade 813, a shaft 821, a front bracket 819, a rear bracket 817, a bladder 809, and a tube 803, and a second occluder including an occluder blade 814, a shaft 820, a front bracket 818, a rear bracket 816, a bladder 808, and a tube 804. The rear brackets 816 and 817 are mounted to the enclosure top 802 via shaft 825, blocks 826 and 827, and clamps 828 and 829. The rear brackets 816 and 817 are held in a substantially fixed position, although the rear brackets 816 and 817 are able to rotate about the shaft 825 as needed for operation of the occluders. The front bracket 819 is mounted to the enclosure top 802 via shaft 821 and sliding blocks 823 and 824, while the front bracket 818 is mounted to the enclosure top 802 via shaft 820 and sliding blocks 822 and 823. The front brackets 818 and 819 are able to slide forward and backward along channels formed in the sliding blocks 822, 823, and 824 as needed for operation of the occluders. The occluder blades 813 and 814 can be manually retracted if necessary. The edge of the occluder blades 813 and 814 that engages the tubing are typically rounded so as not to cut or crease the tubing.

Chassis Components

The chassis components 414 include various mechanical hardware components that are not considered part of the other assemblies. Among other things, the chassis components 414 include the DC air pump 511, a chassis base, a door sensor (and cable), mounting foot grommets, skins (housing), and associated hardware and fasteners. The housing includes a mounting point, on the back of the unit, for the manual piston bladder (door) vent 503.

Pump Cassette Handling

Figure 12:
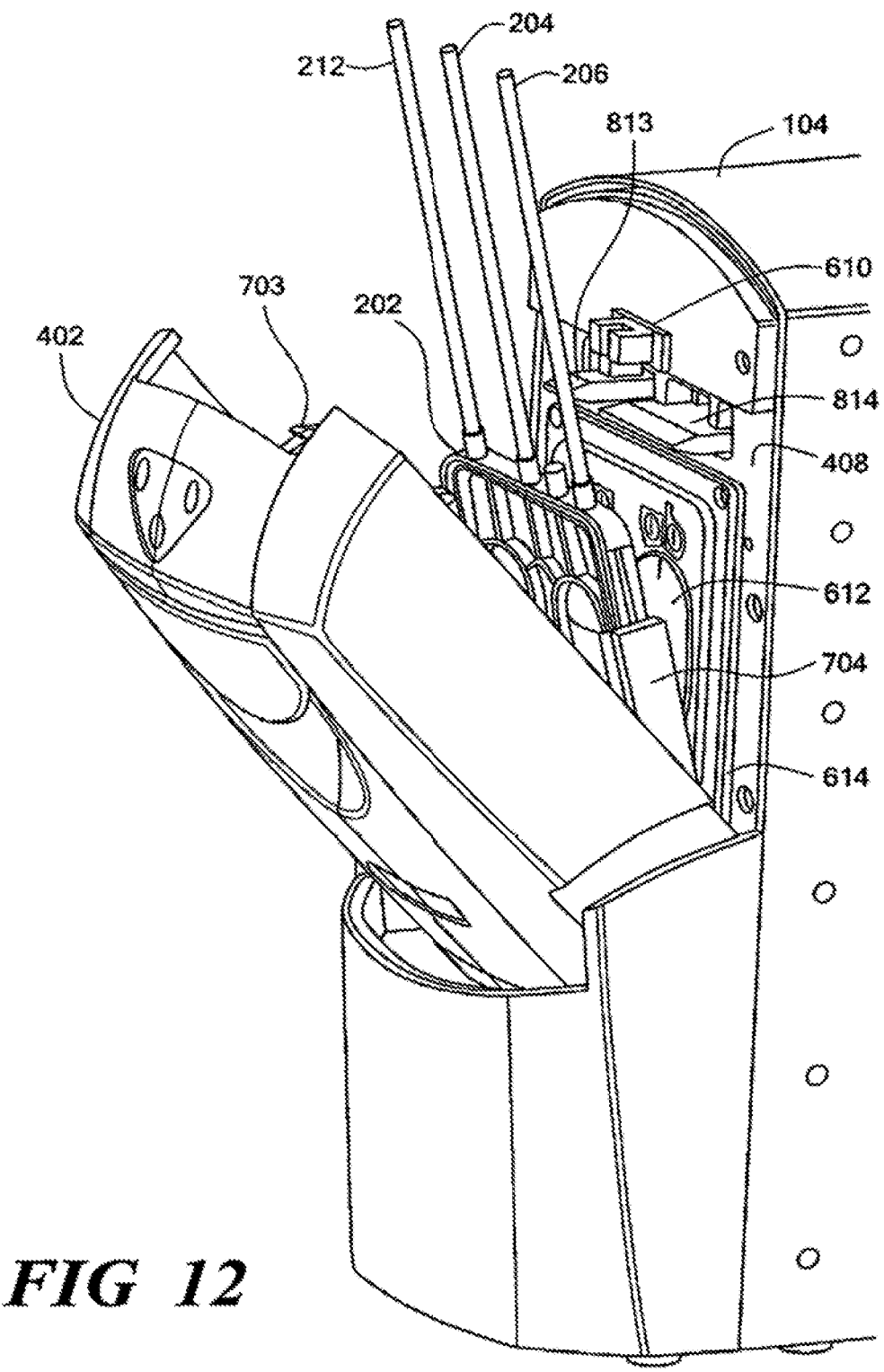
FIG. 12 is a schematic diagram showing the pump cassette installed in the blood pump in accordance with an embodiment of the present invention.

FIG. 12 is a schematic diagram showing the pump cassette 202 installed in the blood pump 104 in accordance with an embodiment of the present invention. The pump cassette 202 is installed in the cassette receptacle 704. The door assembly 402 will only close if the pump cassette 202 is oriented correctly in the cassette receptacle 704, and will not close if the pump cassette 202 is inserted backwards so that the tubing connected to the pump cassette 202 does not align with corresponding channels in the door latch 703. When the door assembly 402 is closed and the bladder in the door assembly 402 is inflated, the pump cassette 202 is pressed tightly against the bezel gasket 612 and gasket retainer 614 on the control assembly 408, the RBCC inlet tube 204 is captured by the air-in-line sensor 610 on the control assembly 408, the occluder blade 813 aligns with and occludes the working solution distribution tube 212, and the occluder blade 814 aligns with and occludes both the RBCC inlet tube 204 and the incubation solution outlet tube 206.

Manual Teardown

During normal blood pump teardown, the blood pump 104 receives commands from the process controller 120 to release pressure against the pump door so that the door can be opened by the operator. The pressure against the door comes from both the door piston bladder and the occluders. While the door piston bladder is pressurized and the tubing occluders are engaged, it is virtually impossible for the operator to open the pump door and remove the pump cassette. If communication between the process controller 120 and the blood pump 104 is lost, then the operator will need to relieve this pressure manually in order to remove the cassette. Among other things, this involves the operator pressing the manual door release valve on the back of the pump to deflate the bladder in the door assembly. The operator may also manually retract the occluders if necessary.

It should also be noted that the flow diagrams are used herein to demonstrate various aspects of the invention, and should not be construed to limit the present invention to any particular flow or implementation. In some cases, certain process steps can be omitted or performed in a different order than shown without changing the overall results or otherwise departing from the true scope of the invention.

The present invention may be embodied in other specific forms without departing from the true scope of the invention. The described embodiments are to be considered in all respects only as illustrative and not restrictive.

What is claimed is:

1. A disposable set of n interconnected pump cassettes comprising:
   a first infusion line to the set connected to a distribution line of the set that has n branches, each branch connected to a respective first inlet of each of the n pump cassettes;
   n second infusion lines to the set, each one of the n second infusion lines configured to connect one of n separate solution sources to a respective one of n second inlets of the n pump cassettes;
   each one of the n pump cassettes comprising a first and a second pumping chamber, wherein for each pump cassette of the n pump cassettes:
   wherein the first inlet of each pump cassette connects via a single valve only to the first pumping chamber, and the second pumping chamber has a valved connection to the second inlet of each of the n pump cassettes, an outlet of the first pumping chamber has a valved connection to the second pumping chamber, and an outlet of the second pumping chamber has a valved connection to an outlet of each of the n pump cassettes; each one of the outlets of the n pump cassettes is connected to a respective one of n containers via a flexible line, each container configured to receive a mixture of fluid from the first inlet and the second inlet of a pump cassette to which said container is connected.

2. The disposable set of claim 1, wherein each one of said n pump cassettes includes a vent in valved connection with the first or second pumping chamber.

3. The disposable set of claim 2, wherein each said pumping chamber comprises a flexible membrane configured to pump fluid in and out of the pumping chamber, and configured to mate with a base unit that provides positive or negative pneumatic actuation pressure to the flexible membrane.

4. The disposable set of claim 2, wherein each of the n second infusion lines is configured to connect to a container holding a mixture of red blood cells.

5. The disposable set of claim 2, wherein the first infusion line is configured for connection to a container of incubation fluid for mixing with each of the n solution sources.

6. The disposable set of claim 1, wherein each said pumping chamber comprises a flexible membrane configured to pump fluid in and out of the pumping chamber, and configured to mate with a base unit that provides positive or negative pneumatic actuation pressure to the flexible membrane.

7. The disposable set of claim 1, wherein each of the n second infusion lines is configured to connect to a container holding a mixture of red blood cells.

8. The disposable set of claim 7, wherein the first infusion line is configured for connection to a container of incubation fluid for mixing with each of the n solution sources.

9. The disposable set of claim 1, wherein the first infusion line is configured for connection to a container of incubation fluid for mixing with each of the n solution sources.

10. The disposable set of claim 1, wherein for each pump cassette of the n pump cassettes, the outlet of the first pumping chamber has a valved connection to a flowpath in the pump cassette, the flowpath having a valved connection to an inlet or the outlet of the second pumping chamber.

11. A disposable set of n interconnected pump cassettes comprising:
    a first infusion line to the set connected to a distribution line of the set that has n branches, each branch connected to a respective first inlet of each of the n pump cassettes;
    n second infusion lines to the set, each one of the n second infusion lines configured to connect one of n separate solution sources to a respective one of n second inlets of the n pump cassettes;

each one of the n pump cassettes comprising a first and a second pumping chamber, wherein for each pump cassette of the n pump cassettes:

wherein the first inlet of each cassette connects via a single valve only to the first pumping chamber, and the second pumping chamber has a valved connection to the second inlet of each of the n pump cassettes, an outlet of the first pumping chamber has a valved connection to the second pumping chamber, and an outlet of the second pumping chamber has a valved connection to an outlet of each of the n pump cassettes; each one of the outlets of the n pump cassettes is connected to a respective one of n containers via a flexible line, each container configured to receive a mixture of fluid from the first inlet and the second inlet of a pump cassette to which said container is connected; and wherein each said pumping chamber comprises a flexible membrane configured to pump fluid in and out of the pumping chamber, and configured to mate with a base unit that provides positive or negative pneumatic actuation pressure to the flexible membrane.

12. The disposable set of claim 11, wherein each one of said n pump cassettes includes a vent in valved connection with the first or second pumping chamber.

13. The disposable set of claim 11, wherein each of the n second infusion lines is configured to connect to a container holding a mixture of red blood cells.

14. The disposable set of claim 13, wherein the first infusion line is configured for connection to a container of incubation fluid for mixing with each of the n second solution sources.

15. The disposable set of claim 11, wherein the first infusion line is configured for connection to a container of incubation fluid for mixing with each of the n solution sources.

16. The disposable set of claim 11, wherein for each pump cassette of the n pump cassettes, the outlet of the first pumping chamber has a valved connection to a flowpath in the pump cassette, the flowpath having a valved connection to an inlet or the outlet of the second pumping chamber.

* * * * *